(12) United States Patent
Merlo

(10) Patent No.: US 7,009,194 B2
(45) Date of Patent: Mar. 7, 2006

(54) METHOD FOR MOUNTING RADIATION TREATMENT BLOCKS ON A RADIATION TREATMENT BLOCK MOUNTING PLATE, AN ADJUSTABLE RADIATION TREATMENT BLOCK MOUNTING TRAY AND A TEMPLATE AND METHOD FOR MAKING A FORM FOR CASTING A RADIATION TREATMENT BLOCK

(76) Inventor: Clifford J. Merlo, 722 Kingman Ave., Santa Monica, CA (US) 90402

( * ) Notice: Subject to any disclaimer, the term of this patent is extended or adjusted under 35 U.S.C. 154(b) by 158 days.

(21) Appl. No.: 10/696,372

(22) Filed: Oct. 28, 2003

(65) Prior Publication Data

US 2005/0087703 A1    Apr. 28, 2005

(51) Int. Cl.
*G21K 1/02*    (2006.01)
*G21F 5/04*    (2006.01)

(52) U.S. Cl. .............................. 250/505.1; 250/515.1; 378/147; 378/152; 378/153; 378/65

(58) Field of Classification Search ............. 250/505.1, 250/515.1; 378/65, 147, 152, 153
See application file for complete search history.

(56) References Cited

U.S. PATENT DOCUMENTS

| | | | |
|---|---|---|---|
| 4,158,779 A | | 6/1979 | Rommel et al. |
| 4,598,208 A | | 7/1986 | Brunelli et al. |
| 4,707,846 A | | 11/1987 | Sportelli et al. |
| 4,798,961 A | | 1/1989 | Augustsson |
| 4,868,844 A | * | 9/1989 | Nunan ................ 378/152 |
| 5,056,128 A | | 10/1991 | Thompson |
| 5,360,666 A | | 11/1994 | Eichmiller |
| 5,438,991 A | * | 8/1995 | Yu et al. .............. 600/426 |
| 5,550,383 A | | 8/1996 | Haskell |
| 5,866,914 A | | 2/1999 | Jones |
| 5,892,238 A | | 4/1999 | Hutner et al. |
| 6,052,436 A | | 4/2000 | Huttner et al. |
| 6,320,938 B1 | | 11/2001 | Hopper |
| 6,377,661 B1 | | 4/2002 | Guru et al. |
| 6,526,123 B1 | | 2/2003 | Ein-Gal |
| 2003/0123609 A1 | | 7/2003 | Manske |
| 2003/0128812 A1 | | 7/2003 | Appleby et al. |

OTHER PUBLICATIONS

MEDTEC catalog web page for Blocking Trays located at http://medtec.com/products/moldroom/consumables/MT-CB-BLT.htm.

(Continued)

*Primary Examiner*—Nikita Wells
(74) *Attorney, Agent, or Firm*—Lord, Bissell & Brook; James H. Wynn; Roberta L. Hastreiter

(57) ABSTRACT

The present invention provides processes and apparatuses for mounting radiation treatment blocks on a radiation treatment block mounting plate, adjusting a radiation treatment block in a radiation treatment beam and forming a radiation treatment block. The present invention provides a method of mounting a radiation treatment block on a radiation treatment block mounting plate that minimizes or eliminates the creation of toxic and hazardous dust and waste and radiation treatment block misalignment problems. The apparatuses and processes of the present invention also provide an adjustable radiation treatment block mounting tray and method for easily and precisely adjusting a radiation treatment block to a radiation beam for the prescribed treatment of a patient.

The present invention further provides apparatuses and methods for forming a radiation treatment block using a template with the perimetric outline of different sized radiation treatment blocks with a commercially-available foam block cutting machine to make a foam mold for casting a radiation treatment block.

198 Claims, 11 Drawing Sheets

OTHER PUBLICATIONS

MEDTEC catalog web page for Tray Adapters located at http://medtec.com/products/misc/MT-Tray.htm.

Bionix Radiation Therapy catalog web page for Blocking Trays located at www.BionixRT.com.

Radiation Products Design, Inc. catalog web page for Shielding Devices and Eye Applicators located at http://www.rpdinc.com/html/untitled 530.html.

Radiation Products Design, Inc. catalong web page for Custom Block Trays located at http://rpdinc.com/html/untitled 499.html.

* cited by examiner

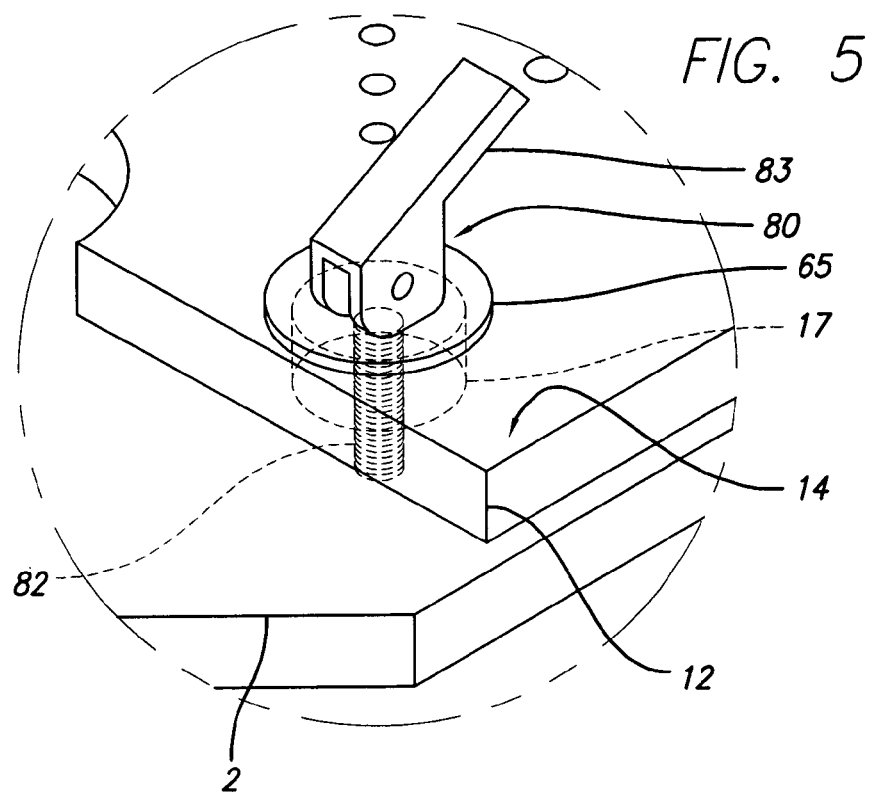
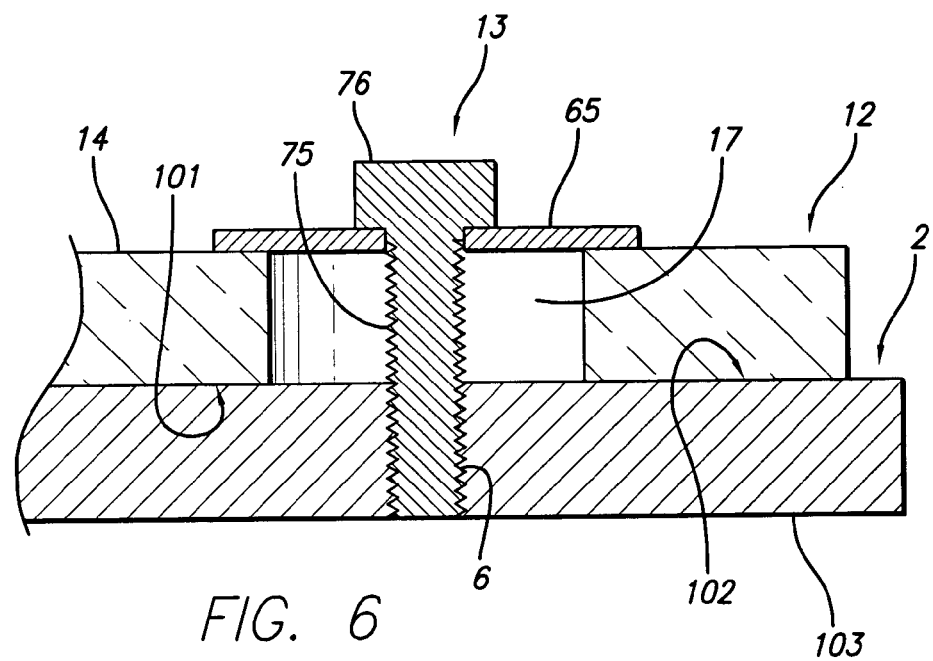

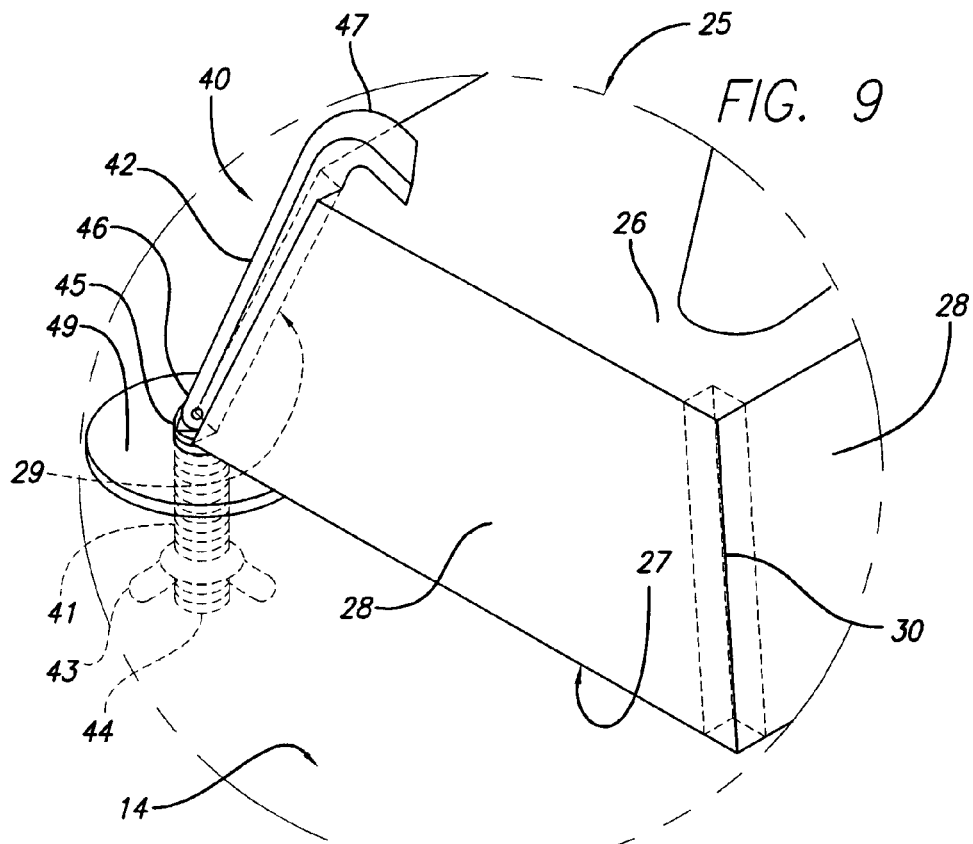
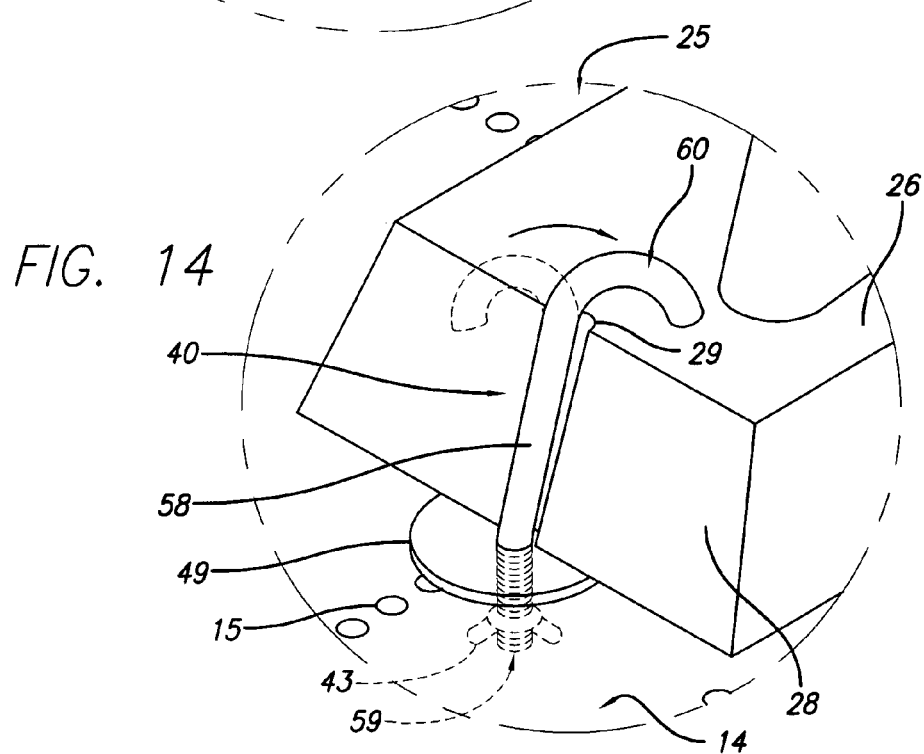

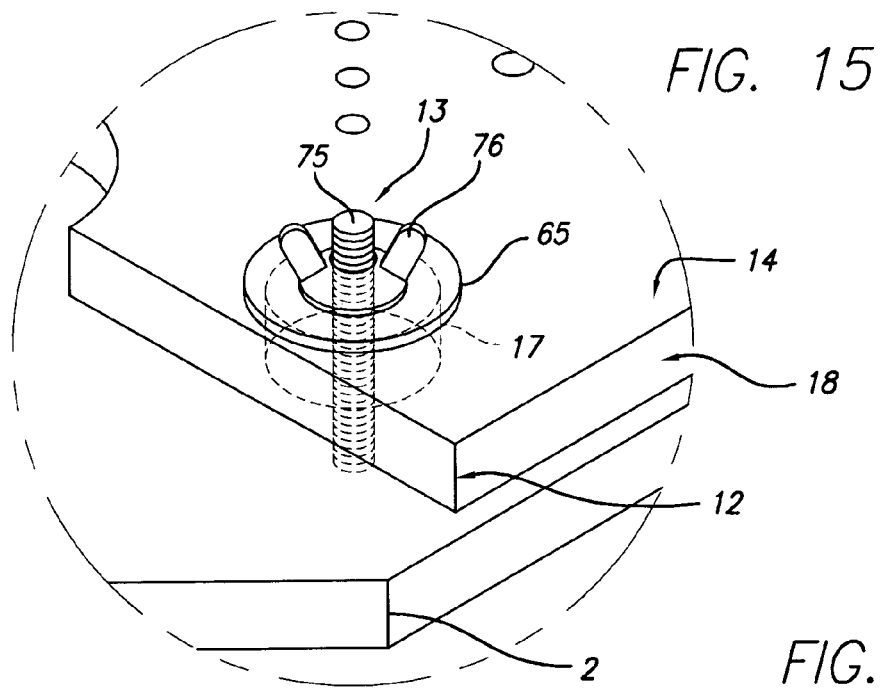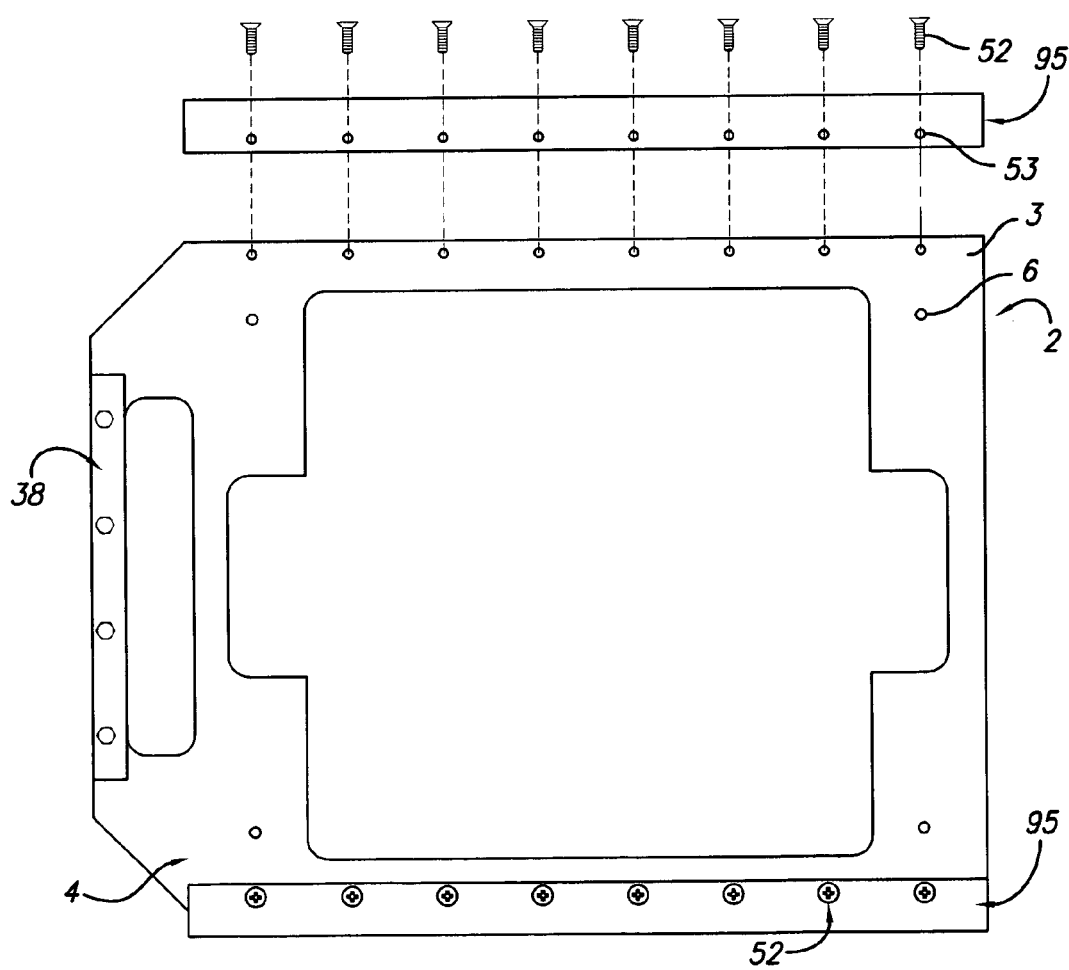

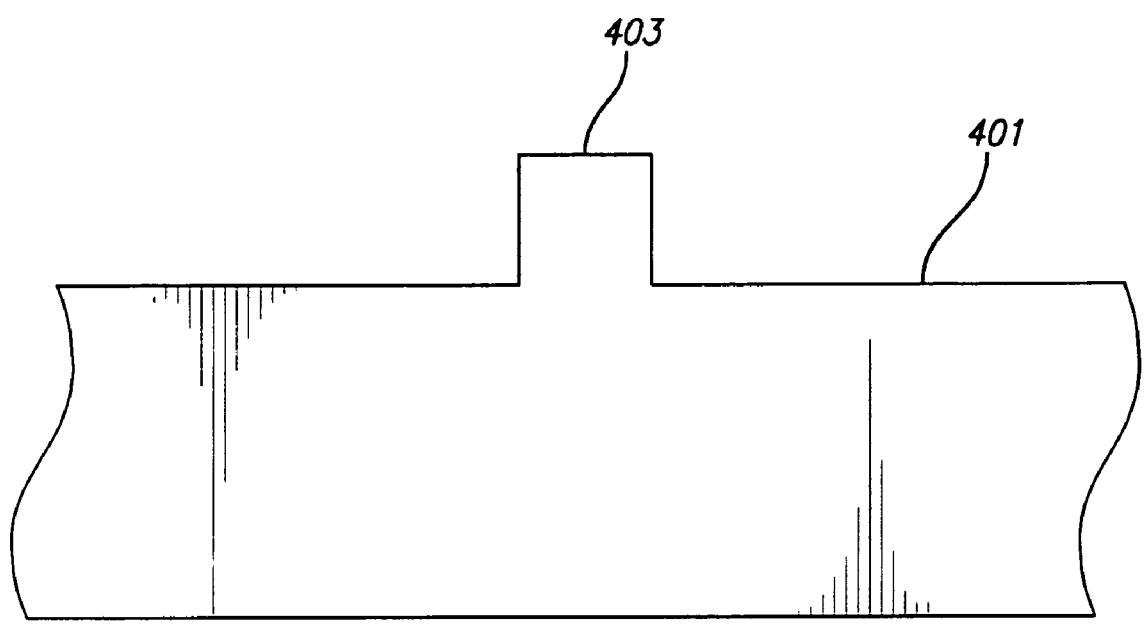
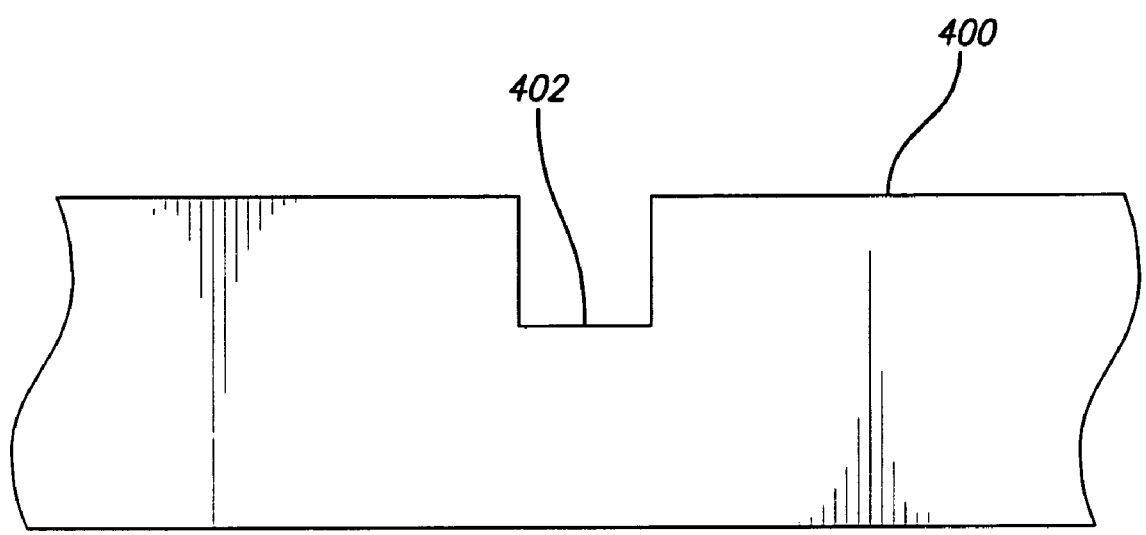
FIG. 19

METHOD FOR MOUNTING RADIATION TREATMENT BLOCKS ON A RADIATION TREATMENT BLOCK MOUNTING PLATE, AN ADJUSTABLE RADIATION TREATMENT BLOCK MOUNTING TRAY AND A TEMPLATE AND METHOD FOR MAKING A FORM FOR CASTING A RADIATION TREATMENT BLOCK

BACKGROUND OF THE INVENTION

1. Field of the Invention

The present invention relates to the area of medicine known as radiation oncology which uses radiation to treat cancer and, more specifically, to a method for mounting radiation treatment blocks on a radiation treatment block mounting tray, an adjustable radiation block mounting tray and a template and method for making a form for casting a radiation treatment block.

2. Description of Related Art and Other Considerations

Radiation produced in a machine and directed towards cancer in humans and animals was found to be effective by the early 1900's. Original machines did not have apertures to control the size of the radiation beam, but later improvements in the form of blocking apertures were placed around the radiation beam to reduce the size of the emanating beam and to provide some protection to uninvolved body structures and anatomy of the patient. The ability to provide protection to uninvolved body structures is highly desirous and allows physicians to increase the radiation dose with the aim of obtaining enhanced results in the treatment of the cancer. To that end, radiation treatment blocks were developed.

Radiation treatment blocks are blocks of metal placed in the path of the radiation beam to shape the radiation beam so that the beam is applied to the prescribed area of treatment for the patient. Historically, radiation blocks were produced in standard shapes without regard to the specific anatomy of a patient. This often required that multiple blocks be utilized to shape the radiation beam to the desired field. This is labor intensive as typically the blocks are heavy. Also, because the blocks were available only in preformed geometric shapes, it also made it difficult to precisely shape the radiation beam to the anatomy of each patient.

More recent technology allows a radiation treatment block to be custom fabricated to precisely shape the radiation beam to a specific patient's anatomy. However, even with the development of custom fabricated radiation treatment blocks, problems with mounting and adjusting the blocks within the radiation beam have persisted. The present methods and apparatuses solve these problems.

Custom blocking structures, or radiation treatment blocks, must be tailored to precisely fit patients and their anatomies. Therefore, for each patient, each block is cut or configured with an aperture which is precisely shaped to "fit" the specific patient's anatomy and is placed in the path of the radiation treatment beam to provide further protection to uninvolved anatomy, thereby allowing even higher doses of radiation to be delivered to the cancer. As higher and higher doses are administered to the patient, the exact position of these blocks in the beam is of paramount importance, because even small deviations of the block aperture and, thus, the beam configuration can lead to permanent, irreversible damage to uninvolved anatomy of the patient.

There are several conventionally employed block positioning techniques and devices for shaping the radiation beam, but all have deficiencies as more fully discussed below, such as block misalignment and inaccurate positioning, the potential for radiation contamination of the treatment facility with toxic and carcinogenic heavy metals, and creating environmentally toxic waste.

A. Misalignment/Inaccuracy Problems

Currently, blocks are typically set on a clear plastic plate known as a block mounting tray or plate, which fits into the radiation treatment machine. The block is typically held in position by gravitational force when the tray is in its horizontal position with respect to the treatment machine. Typically, a radiation technologist, that is the person who administers the radiation to the patient on a day-to-day basis, places and aligns the block each day by hand. This is a tedious, time-consuming procedure, which often results in significant day-to-day variation in positioning the block, all of which are undesirable. Due to the constant handling of radiation treatment blocks by the technologist, there is a potential for the technologist to be exposed to the toxic heavy metals in the block.

An article entitled "Potential Exposure to Metal Fumes, Particulates, and Organic Vapors During Radiotherapy Shielding Block Fabrication" appearing in the September/October 1986 edition of *Medical Physics* identified potential hazards to block handling personnel as including: (1) bruises to hands or feet from dropped blocks, (2) inhalation of metallic dust particles and fumes, (3) ingestion of metal alloy, (4) skin absorption of metal alloy, and (5) lifting hazards posed by placing very heavy blocks into position.

When the tray is in a more vertical position and, therefore, not supported by the block mounting tray, the block will move or slide off of the tray unless the block is held onto the tray. Accordingly, various methods and devices have been used to mount the block to the tray. The most widely-used method involves the drilling of a hole in the bottom of the block and screwing it to the tray with a simple sheet metal screw. However, many technologists have difficulty in performing this task because it requires a certain degree of skill and careful positioning of the block on the tray, and the effective use of a drill and sheet metal screws. In addition, because the metals and alloys most commonly utilized to form the block are relatively soft, the screw threads in the block can easily be stripped, making it difficult to securely affix the block to the tray. The result is often that the block is poorly secured to the tray, and is loose and slightly misaligned with respect to the beam.

Efforts to correct these problems create further difficulties. When a block is misaligned but fixed to the tray, some technologists often simply compensate for the misalignment by moving the patient, who is already laying or positioned on the treatment machine, with respect to the beam. However, such movement of the patient may create an aberration in the geometry calculated for the treatment and result in a significant change in the dose of radiation delivered to the patient. Furthermore, such compensation may not be communicated to another technologist who provides subsequent treatment. As a result, uninvolved structures or radiation sensitive body parts in the patient may be over-irradiated and permanently damaged.

Other technologists, when confronted with a fixed, but misaligned block, usually elect to cancel treatment on that day and have the patient return for treatment on a subsequent day, after the tray has been dismantled and the block re-affixed to the tray. Such cancellation results in wasted time and effort for both the patient and the technologist, including lost treatment days for the patient. In addition, this subsequent effort to re-affix the block to the tray may also result in a misaligned block. Remounting the block also requires additional handling of the block, which increases the risk that the radiation technologist may be exposed to the toxic metals that are present in the block.

Another method, in an effort to improve the alignment of the block with respect to the tray, involves the milling of slots through the tray. With this method, the sheet metal screw is loosened, the block is slid with respect to the tray, and the screw is then retightened. This procedure allows the block to be adjusted in one direction, with the goal of regaining the proper alignment. Unfortunately, because such milled slots allow an adjustment in only a single direction, their use does not allow the block to be adjusted in a direction perpendicular to that of the slots. Furthermore, the milling of intersecting perpendicular slots in a tray may weaken its structural integrity and, because the blocks are relatively heavy, they can cause the tray to sag, resulting in the misalignment of the block or even fracture, possibly causing injury to the patient or attending personnel.

A less-commonly used system to affix a block to a tray involves the use of a double-sided, adhesive, foam tape. This system suffers from the alignment-of-the-tray-to-block problem described above, as well as from an inability to adjust the block once it is fixed to the tray. In addition, it is possible that a block, which can weigh as much as twenty-five pounds, could fall on a patient or a technologist, which renders this tape-fixing system a less-favored solution due to safety concerns.

B. Contamination of the Radiation Treatment Facility

In addition to the above-described problems, most blocks are formed from an alloy of toxic heavy metals, specifically lead and cadmium, both of which have known health risks. Cadmium is also known to be highly carcinogenic. The repeated handling of these blocks potentially exposes the technologists to these toxic and carcinogenic metals. Additionally, any drilling of them creates an even greater health risk in the form of fine toxic and carcinogenic dust which, without proper handling, can rapidly permeate the radiation treatment facility and, thus, create a hazardous environment for patients and personnel within the facility.

A variation of the sheet-metal-screw method described above is directed to avoid the drilling of the block and, therefore, the contamination of the radiation treatment facility. In this variation, a sheet metal screw is sunk into the alloy while it is still molten to form a properly molded hole. Once the alloy has solidified, the sheet metal screw is removed and replaced by a shorter sheet metal screw for securing the block to the tray. Although this method avoids the generation of fine, toxic dust from drilling, it still suffers from the other disadvantages of the previously-described method, that is, the metal of the block being softer than the metal of the screw creates the chance that the threads produced in the block can become stripped, which can cause misalignment of the block or result in the block falling off the tray and injuring the patient or technologist. Correction of misalignment problems is difficult and time consuming. If the threads become stripped, a new block has to be cast and/or a new hole has to be drilled. If a new hole is drilled, toxic shavings and dust are created.

C. Environmentally Toxic Waste

Another known method to affix a block to a tray is by sinking a one or more threaded rod into the molten alloy while the alloy is in the block forming mold. After the alloy has cooled a nut can be screwed onto each threaded rod protruding through a hole or slot in the tray in order to affix the block to the tray. This technique again requires an alignment of the tray to the block and can result in possible misalignment inaccuracies due to a single attachment point when one rod is used which can allow the block to shift or rotate on the tray. If more than one rod is used it creates multiple attachment points which makes it difficult to adjust the position of the block on the tray. Furthermore, after the block is no longer needed, the block is melted, whereupon each threaded rod will float to the top of the molten alloy where they can be retrieved. Retrieved threaded rods, however, are usually coated with solidified hazardous alloy or metals and are therefore, unusable. As a result, the rods must be disposed of in accordance with environmental regulations. This creates additional hazardous materials that must be disposed of at licensed disposal facilities. Proper disposal of toxic materials is both costly and time consuming for the facility staff due to the documentation required by environmental regulations. In the past, improper disposal of toxic metals into the general waste system of the local municipality has resulted in toxic pollution to the environment. As an example, many species of trees and the white-tailed ptarmigan of the Rocky Mountains have thereby been exposed to cadmium toxicity as a result of improper disposal or containment of materials containing cadmium.

D. Current Radiation Block Forming Techniques

Currently, radiation treatment blocks are typically prepared by a technologist drawing the perimetric outline of a block around a prescribed treatment area that has been drawn on an x-ray film of a patient by an oncologist. The technologist first draws the outline of the appropriate size radiation treatment block and then traces that pattern on a foam block cutting machine to cut the outline of a radiation treatment block. This procedure is difficult because the technologist has to decide on the correct perimetric outline of a block and oftentimes has no specific guidelines for making the decision. As a result, the sides of a resultant block are oftentimes not square, not properly oriented and of insufficient thickness resulting in the radiation beam spilling over the outer edge of the block. This can result in radiation being applied to uninvolved structures and patient anatomy. The template of the present invention allows a technologist to overlay a template on the marked x-ray film or vice versa. The technologist then can readily observe the appropriate perimetric outline on the template and simply trace the outline using the stylus of the foam block cutting machine. A hot wire present in the machine cuts the perimetric outline of the foam block to correspond with the perimetric outline on the template. A designated beam shaping area can also be cut within the body of the block that will shape the radiation beam for the prescribed treatment. The use of the template saves the technologist time in the preparation of a form for casting a radiation treatment block. The template optionally also provides notches on the sides and corners of the perimetric outlines of the blocks.

Tracing of the notches with the stylus of the foam block cutting machine when the perimetric outline of the block is being cut in the foam block will create notches in the block when it is cast. The notches in the block will accept the shaft of a clamping device of the present invention to assist in aligning and clamping a block to a mounting tray or plate.

E. Description of the Art

The patent literature includes a description of technology encompassing the above-described problems.

U.S. Pat. No. 5,115,139 ("Cotter patent") discloses a slotted bracket attached to the underside of a block, through which a connecting bolt passes to run in a slot milled into a tray. The device of the Cotter patent allows the block to be adjusted in a lateral direction and to rotate the block on the tray. However, the device disclosed in the Cotter patent is not applicable to most modern blocks now commonly used, which are specifically cast to match the anatomy of a unique patient undergoing treatment. Furthermore, the device involves only a single point-of-attachment for these heavy blocks that allows for possible unintended rotation or migration of the block on the tray under the influence of gravity. The device also requires that holes be drilled into or cast into the block. If holes are drilled, the Cotter device creates toxic metal dust and particulate matter. If the holes are drilled or cast, they are prone to stripping due to the softness of the metal that is most commonly used to form the blocks.

U.S. Pat. No. 4,266,139 ("'139 patent") describes a base plate that moves in parallel mounting rails. The device disclosed in the '139 patent allows a plate with a masking overlay to be mounted on a radiation machine. The device, however, does not allow precise multidirectional adjustment of the masking overlay. In addition, the device uses Velcro strips to attach thin metal shield plates thereto. Such a system is incompatible with most custom cast blocks in use today, which can be very heavy and would raise safety concerns if the block fell from the tray.

U.S. Pat. No. 4,472,637 ("'637 patent") discloses a base plate that can be mounted in slots on a radiation machine. The device allows only bi-directional movement of blocking shields. The '637 patent also discloses a shield with a single attachment point which can be prone to misalignment or rotational movement of the shield on the tray resulting in inaccurate and potentially injurious treatment of the patient.

U.S. Pat. No. 5,056,128 ("'128 patent") discloses a metal base plate and allows the magnetic mounting of radiation shielding devices. The apparatus would likely not work with the radiation treatment blocks currently in use because: (1) they are not magnetic, and (2) the size and weight of the blocks may make magnetic mounting unsafe.

U.S. Pat. No. 4,700,451 ("'451 patent") describes a method for indexing a block to a tray. The method, however, uses screws to attach the custom cast block to the tray. This method requires that holes be drilled into the block to secure the screws. This creates toxic dust and particulate matter which exposes technologists to toxic metal. This method also creates the potential for the screws to strip out of the holes resulting in possible misalignment of the block or could result in the block falling off the tray and injuring a patient or technologist.

BRIEF SUMMARY OF THE INVENTION

The method for mounting a radiation treatment block on a radiation treatment block mounting tray of the present invention comprises providing a radiation treatment block mounting plate, providing a radiation treatment block for mounting on the plate, providing a plurality of external clamping devices to secure the block to the plate, securing the external clamping devices to the plate, and securing the block to the plate by adjusting the external clamping devices.

An adjustable radiation treatment block mounting tray of this invention is comprised of a substantially rigid frame body, a plate, and one or more releasable fastener to releasably secure the plate to the frame body when at least one releasable fastener is in a fastened position and to allow the plate to move relative to the frame body when each fastener is in a released position. More specifically, in one embodiment of the invention, orifices are drilled or otherwise formed into the plate. A releasable fastener, such as a thumbscrew, is positioned through each orifice for holding the plate to the frame body. The orifices allow the plate to move in any direction on the surface of the frame body, thereby allowing the desired adjustment of the radiation treatment block in any direction when the fasteners are in a released position.

A method for adjusting a radiation treatment block in a radiation treatment beam of this invention comprises providing a radiation treatment block mounted on an adjustable radiation treatment block mounting tray with releasable fasteners to releasably secure the plate of the tray to the frame body of the tray. The tray is mounted in a radiation treatment machine. The block can be aligned within the radiation treatment beam by adjusting the releasable fasteners to a released position allowing the plate and the block to move relative to the frame body. The plate is moved until the block is correctly aligned within the radiation beam for treatment of the patient. The releasable fasteners can be adjusted to a fastened position compressibly securing the plate to the frame body, thereby securing the block within the radiation beam.

A template of this invention for use with a foam block cutting machine for making a form to cast a radiation treatment block comprises a transparent sheet or plate having perimetric outlines of radiation treatment blocks of varying sizes marked or inscribed thereon. A method of this invention for making a foam form to cast a radiation treatment block comprises using a template with the perimetric outlines of varying sizes of radiation treatment blocks with a commercially-available foam block cutting machine to cut the perimetric outline of a radiation treatment block.

Other objects and advantages, as well as a more complete understanding of the present invention, will appear from the following explanation of preferred embodiments and the accompanying drawings thereof.

BRIEF DESCRIPTION OF THE DRAWINGS

FIG. 5 is a partial view of the tray of the current invention showing a cam clamp as the releasable fastener used to releasably secure a plate to the frame body of the tray.

FIG. 6 is a section view showing a preferred embodiment of the releasable fastener.

FIG. 9 shows an alternative embodiment of a radiation treatment block having grooves at the corner edges of the block.

FIG. 14 is a partial view showing an alternative embodiment of a clamping device having a bent shaft.

FIG. 15 shows an alternative embodiment of a releasable fastener comprising a rod with threaded end portions, a washer, and a threaded nut.

FIG. 16 shows the frame body of a tray of the invention having a rail mounted thereon.

FIG. 19 shows a ruler that can be used to draw perimetric outlines on a template of the invention.

Figure 1:
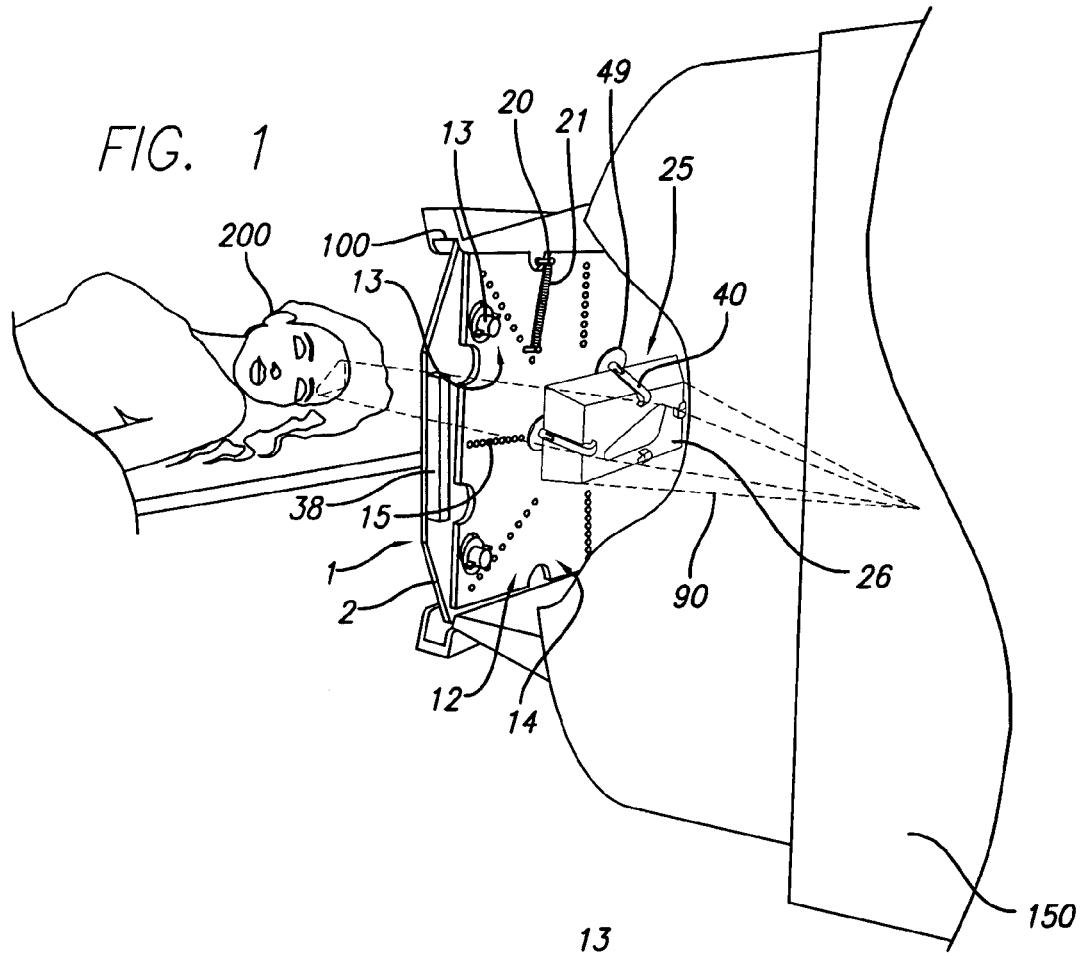
FIG. 1 is a perspective view of a tray of the current invention inserted into a radiation treatment machine and a typical treatment of a patient with radiation.

Specific apparatuses and methods within the scope of the present invention include, but are not limited to, the apparatuses and methods discussed in detail herein and/or illustrated in the drawings that are present herein.

Contemplated equivalents of the apparatuses and methods described and illustrated herein and/or illustrated in the drawings contained herein include apparatuses and methods which otherwise correspond thereto, and which have the same general properties and/or components thereof, wherein one or more simple or other variations of components, materials or steps are made.

All of the structures and components used in the apparatuses and methods of the current invention and to carry out the methods of the present invention, are commercially-available from sources known by those of ordinary skill in the art.

The different components and structures that may be employed in the methods and apparatuses of the present invention may be generally arranged in the manner shown in the drawings, or described hereinbelow. However, the present invention is not limited to methods and apparatuses shown in the drawings and specifically described herein having the precise arrangements, configurations, dimensions and/or instrumentalities shown in these drawings, or described hereinbelow. These arrangements, configurations, dimensions and instrumentalities may be otherwise, as circumstances require.

Different specific embodiments of that may be employed in the methods and apparatuses of the present invention will now be described with reference to the drawings.

DETAILED DESCRIPTION

Some Preferred Embodiments

In a first aspect the present invention provides for a method for mounting at least one radiation treatment block on a radiation treatment block mounting plate comprising:

(a) providing at least one radiation treatment block, said radiation treatment block having a top surface, a bottom surface and at least one side surface;

(b) providing a radiation treatment block mounting plate, said radiation treatment block mounting plate having an upper face, a lower face and at least one mounting hole or slot that extends at least partially through the radiation treatment block mounting plate from its upper surface, and wherein said mounting hole or slot is positioned to permit radiation treatment blocks having different sizes to be affixed to said radiation treatment block mounting plate;

(c) providing at least one affixing means for compressibly affixing said radiation treatment block to said radiation treatment block mounting plate, wherein said affixing means has an upper portion and a lower portion;

(d) placing the bottom surface of said radiation treatment block on said upper face of said radiation treatment block mounting plate;

(e) attaching said upper portion of said affixing means to said radiation treatment block;

(f) placing said lower portion of said affixing means through said mounting hole or slot present in said radiation treatment block mounting plate;

(g) securing said lower portion of said affixing means to said radiation treatment block mounting plate; and (h) adjusting said affixing means to compressibly and releasably affix said radiation treatment block to said radiation treatment block mounting plate.

In a second aspect the present invention provides for a method for mounting at least one radiation treatment block on a radiation treatment block mounting plate comprising:

(a) providing a radiation treatment block mounting plate, said radiation treatment block mounting plate having an upper face and a lower face and at least one mounting hole or slot extending through said radiation treatment block mounting plate from said upper face to said lower face for receiving one or more external clamping means, said mounting hole or slot being positioned to allow radiation treatment blocks having different sizes to be affixed to said radiation treatment block mounting plate;

(b) providing at least one radiation treatment block, said radiation treatment block having a top surface, a bottom surface and at least one side surface;

(c) positioning said bottom surface of said radiation treatment block on said upper face of said radiation treatment block mounting plate;

(d) providing external clamping means for compressibly affixing each radiation treatment block to said upper face of said radiation treatment block mounting plate;

(e) attaching said external clamping means to said radiation treatment block mounting plate;

(f) positioning said external clamping means on each radiation treatment block;

(g) adjusting said external clamping means to compressibly affix said radiation treatment block to said upper face of the radiation treatment block mounting plate.

In a third aspect the present invention provides for a method for mounting a radiation treatment block on a radiation treatment block mounting plate comprising:

(a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;

(b) providing at least one radiation treatment block, said radiation treatment block having a top surface, a bottom surface and at least one side surface;

(c) providing at least one clamping device to externally affix said radiation treatment block to said radiation treatment block mounting plate, at least one clamping device having an end portion sized and shaped to fit within a mounting hole or slot for securing said clamping device to said radiation treatment block mounting plate and an opposite end portion sized and shaped to engage said top surface of said radiation treatment block;

(d) positioning said bottom surface of said radiation treatment block on said upper face of said radiation treatment block mounting plate;

(e) positioning said end portion of said clamping device through a mounting hole or slot and securing said clamping device to said radiation treatment block mounting plate;

(f) positioning said opposite end portion of said clamping device above and adjacent to said top surface of said radiation treatment block; and (g) adjusting said clamping device until at least part of said opposite end portion of said clamping device engages said top surface of said radiation treatment block and compressibly affixes said radiation treatment block to said upper face of said radiation treatment block mounting plate.

In a fourth aspect the present invention provides for a method for mounting a radiation treatment block on a radiation treatment block mounting plate comprising:

(a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;

(b) providing at least one radiation treatment block, said radiation treatment block having a top surface, a bottom surface and at least one side surface;

(c) providing at least one clamping device to externally affix said radiation treatment block to said radiation treatment block mounting plate, wherein at least one clamping device comprises a shaft and a threaded nut, said shaft having a threaded end portion and an opposite end portion sized and shaped to engage said top surface of said radiation treatment block;

(d) positioning said bottom surface of said radiation treatment block on said upper face of said radiation treatment block mounting plate;

(e) inserting said threaded end portion of said shaft through a mounting hole or slot in said radiation treatment block mounting plate, said mounting hole or slot being positioned proximate to at least one side surface of said radiation treatment block;

(f) attaching a threaded nut onto said threaded end portion of said shaft;

(g) positioning said shaft until said opposite end portion of said shaft is positioned above and adjacent to said top surface of said radiation treatment block;

(h) adjusting said threaded nut on said threaded end portion of said shaft until at least part of said opposite end portion of said shaft engages said top surface of said radiation treatment block and compressibly affixes said radiation treatment block to said upper face of said radiation treatment block mounting plate.

In a fifth aspect the present invention provides for a method for mounting a radiation treatment block on a radiation treatment block mounting plate comprising:

(a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;

(b) providing at least one radiation treatment block, said radiation treatment block having a top surface, a bottom surface and at least one side surface, at least one side surface having at least one groove positioned therein, said groove extending from said top surface to said bottom surface and projecting from said side surface into said radiation treatment block, said groove being sized and shaped to allow a shaft of a clamping device to fit at least partially within said groove;

(c) providing at least one clamping device to externally affix said radiation treatment block to said radiation treatment block mounting plate, wherein at least one clamping device comprises a shaft and a threaded nut, said shaft having a threaded end portion and an opposite end portion sized and shaped to engage said top surface of said radiation treatment block;

(d) positioning said bottom surface of said radiation treatment block on said upper face of said radiation treatment block mounting plate;

(e) inserting said threaded end portion of said shaft through a mounting hole or slot in said radiation treatment block mounting plate, said mounting hole or slot being positioned proximate to a groove in a side surface of said radiation treatment block;

(f) attaching a threaded nut onto said threaded end portion of said shaft;

(g) positioning said shaft of said clamping device until said shaft is positioned at least partially in said groove and said opposite end portion of said shaft is positioned above and adjacent to said top surface of said radiation treatment block;

(h) adjusting said threaded nut on said threaded end portion of said shaft until at least part of said opposite end portion of said shaft engages said top surface of said radiation treatment block and compressibly affixes said radiation treatment block to said upper face of said radiation treatment block mounting plate.

In a sixth aspect the present invention provides for a method for mounting a radiation treatment block on a radiation treatment block mounting plate comprising:

(a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;

(b) providing at least one radiation treatment block, said radiation treatment block having a top surface, a bottom surface and at least one side surface;

(c) providing at least one clamping device to externally affix said radiation treatment block to said radiation treatment block mounting plate, at least one clamping device comprising a rod, a shaft, and a threaded nut, said rod having one end portion hingeably connected to said shaft and an opposite threaded end portion, said shaft having an end portion hingeably connected to said rod and an opposite end portion sized and shaped to engage said top surface of said radiation treatment block;

(d) positioning said bottom surface of said radiation treatment block on said upper face of said radiation treatment block mounting plate, (e) inserting said threaded end portion of said rod of said clamping device through a mounting hole or slot in said radiation treatment block mounting plate, said mounting hole or slot being positioned proximate to at least one side surface of said radiation treatment block;

(f) attaching a threaded nut onto said threaded end portion of said rod;

(g) pivoting said shaft of said clamping device until said opposite end portion of said shaft is positioned above and adjacent to said top surface of said radiation treatment block;

(h) adjusting said threaded nut on said threaded end portion of said rod until at least part of said opposite end portion of said shaft engages said top surface of said radiation treatment block and compressibly affixes said radiation treatment block to said upper face of said radiation treatment block mounting plate.

In a seventh aspect the present invention provides for a method for mounting a radiation treatment block on a radiation treatment block mounting plate comprising:

(a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;

(b) providing at least one radiation treatment block, said radiation treatment block having a top surface, a bottom surface, and at least one side surface, at least one side surface having at least one groove positioned therein, said groove extending from said top surface to said bottom surface and projecting from said side surface into said radiation treatment block, said groove being sized and shaped to allow a shaft of a clamping device to fit at least partially within said groove;

(c) providing at least one clamping device to externally affix said radiation treatment block to said radiation treatment block mounting plate, at least one clamping device comprising a rod, a shaft, and a threaded nut, said rod having one end portion hingeably connected to said shaft and an opposite threaded end portion, said shaft having an end portion hingeably connected to said rod and an opposite end portion sized and shaped to engage said top surface of said radiation treatment block;

(d) positioning said bottom surface of said radiation treatment block on said upper face of said radiation treatment block mounting plate;

(e) inserting said threaded end portion of said rod of said clamping device through a mounting hole or slot in said radiation treatment block mounting plate, said mounting hole or slot being positioned proximate to a groove in a side surface of said radiation treatment block;

(f) attaching a threaded nut onto said threaded end portion of said rod;

(g) pivoting said shaft of said clamping device until said shaft is positioned at least partially in a groove in a side surface of said radiation treatment block and said opposite end portion of said shaft is positioned above and adjacent to said top surface of said radiation treatment block;

(h) adjusting said nut on said threaded end portion of said rod until at least part of said opposite end portion of said shaft engages said top surface of said radiation treatment block and compressibly affixes said radiation treatment block to said upper face of said radiation treatment block mounting plate.

In an eighth aspect the present invention provides for a method for mounting a radiation treatment block on a radiation treatment block mounting plate comprising:

(a) providing a radiation treatment block mounting plate, said radiation treatment block mounting plate having an upper face and a lower face, said radiation treatment block mounting plate further having a plurality of mounting holes or slots extending through said radiation treatment block mounting plate from said upper face to said lower face for receiving a clamping device, said mounting holes or slots being positioned to allow radiation treatment blocks having different sizes to be affixed to said radiation treatment block mounting plate;

(b) providing at least one radiation treatment block, said radiation treatment block having a top surface, a bottom surface, and four side surfaces, each side surface having a groove positioned therein, said groove extending from said top surface to said bottom surface and projecting from said side surface into said radiation treatment block, said groove being sized and shaped to allow a shaft of a clamping device to fit at least partially within said groove;

(c) providing four clamping devices to externally affix said radiation treatment block to said radiation treatment block mounting plate, each clamping device comprising a rod, a shaft, and a threaded nut, said rod having one end portion hingeably connected to said shaft and an opposite threaded end portion, said shaft having an end portion hingeably connected to said rod and an opposite substantially hook shaped end portion;

(d) positioning said bottom surface of said radiation treatment block on said upper face of said radiation treatment block mounting plate;

(e) inserting said threaded end portion of each rod of each clamping device through a mounting hole or slot in said radiation treatment block mounting plate, said mounting hole or slot being positioned proximate to a groove in a side surface of said radiation treatment block;

(f) attaching a threaded nut onto said threaded end portion of each rod;

(g) pivoting said shaft of each clamping device until said shaft is positioned at least partially in a groove in a side surface of said radiation treatment block and said substantially hook shaped end portion of each shaft is positioned above and adjacent to said top surface of said radiation treatment block;

(h) adjusting said nut on said threaded end portion of each rod until at least part of each substantially hook shaped end portion of each shaft engages said top surface of said radiation treatment block and compressibly affixes said radiation treatment block to said upper face of said radiation treatment block mounting plate.

In a ninth aspect the present invention provides for a method for mounting a radiation treatment block on a radiation treatment block mounting plate comprising:
(a) providing a radiation treatment block mounting plate, said radiation treatment block mounting plate having an upper face and a lower face, said radiation treatment block mounting plate having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;
(b) providing at least one radiation treatment block, said radiation treatment block having a top surface, a bottom surface and at least three side surfaces, the intersection of a side surface with another side surface forming a corner edge, said radiation treatment block having a groove positioned on at least one corner edge, said groove extending from said top surface to said bottom surface and projecting from said corner edge into said radiation treatment block, said groove sized and shaped to allow a shaft of a clamping device to fit at least partially within said groove;
(c) providing at least one clamping device to externally affix said radiation treatment block to said radiation treatment block mounting plate, said clamping device comprising a rod, a shaft, and a threaded nut, said rod having one end portion hingeably connected to said shaft and an opposite threaded end portion, said shaft having an end portion hingeably connected to said rod and an opposite end portion shaped and sized to engage said top surface of said radiation treatment block;
(d) positioning said bottom surface of said radiation treatment block on said upper face of said radiation treatment block mounting plate;
(e) inserting said threaded end portion of said rod of said clamping device through a mounting hole or slot in said radiation treatment block mounting plate, said mounting hole or slot positioned proximate to a groove in a corner edge;
(f) attaching a threaded nut onto said threaded end portion of said rod;
(g) pivoting said shaft of said clamping device until said opposite end portion of said shaft is positioned above and adjacent to said top surface of said radiation treatment block; and
(h) adjusting said nut on said threaded end portion of said rod until at least part of said opposite end portion of said shaft engages said top surface of said radiation treatment block and compressibly affixes said radiation treatment block to said upper face of said radiation treatment block mounting plate.

In a tenth aspect the present invention provides for a method for mounting a radiation treatment block on a radiation treatment block mounting plate comprising:
(a) providing a radiation treatment block mounting plate, said radiation treatment block mounting plate having an upper face and a lower face, said radiation treatment block mounting plate having a plurality of mounting holes or slots extending through said radiation treatment block mounting plate from said upper face to said lower face for receiving a clamping device, said mounting holes or slots being positioned to allow radiation treatment blocks having different sizes to be affixed to said radiation treatment block mounting tray.
(b) providing at least one radiation treatment block, said radiation treatment block having a top surface, a bottom surface and at least three side surfaces, the intersection of a side surface with another side surface forming a corner edge, said radiation treatment block having a groove positioned on at least one corner edge, said groove extending from said top surface to said bottom surface and projecting from said corner edge into said radiation treatment block, said groove sized and shaped to allow a shaft of a clamping device to fit at least partially within said groove;
(c) providing at least one clamping device to externally affix said radiation treatment block to said radiation treatment block mounting plate, said clamping device comprising a shaft and a threaded nut, said shaft having a threaded end portion and an opposite end portion sized and shaped to engage said top surface of the radiation treatment block;
(d) positioning said bottom surface of said radiation treatment block on said upper face of said radiation treatment block mounting plate;
(e) inserting said threaded end portion of said shaft of said clamping device through a mounting hole or slot in said radiation treatment block mounting plate, said mounting hole or slot positioned proximate to a groove in a corner edge;
(f) attaching a threaded nut onto said threaded end portion of said shaft;
(g) positioning said shaft of said clamping device until said shaft is positioned at least partially in said groove and said opposite end portion of said shaft is positioned above and adjacent to said top surface of radiation treatment block;
(h) adjusting said threaded nut on said threaded end portion of said shaft until at least part of said opposite end portion of said shaft engages said top surface of said radiation treatment block and compressibly affixes said radiation treatment block to said upper face of said radiation treatment block mounting plate.

In an eleventh aspect the present invention provides for a method for mounting a radiation treatment block on a radiation treatment block mounting plate comprising:
(a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving an external clamping device, said mounting hole or slot positioned to allow the mounting of radiation treatment blocks having different sizes to said radiation treatment block mounting plate;
(b) providing at least one radiation treatment block, said radiation treatment block having a top surface, a bottom surface, and at least one side surface, at least one side surface having at least one groove positioned therein, said groove extending from said top surface to said bottom surface and projecting from said side surface into said radiation treatment block, said groove being sized and shaped to allow a shaft of a clamping device to fit at least partially within said groove;
(c) providing at least one clamping device to externally affix said radiation treatment block to said radiation treatment block mounting plate, at least one clamping device comprising a rod, a shaft, and a threaded nut, said rod having one end portion hingeably connected to said shaft and an opposite threaded end portion, said shaft having an end portion hingeably connected to said rod and an opposite oversized end portion, at least one dimension of said oversized end portion being greater than a dimension of said groove;

(d) positioning said bottom surface of said radiation treatment block on said upper face of said radiation treatment block mounting plate;

(e) inserting said threaded end portion of said rod of said clamping device through a mounting hole or slot in said radiation treatment block mounting plate, said mounting hole or slot being positioned proximate to a groove in a side surface of said radiation treatment block;

(f) attaching a threaded nut onto said threaded end portion of said rod;

(g) pivoting said shaft of said clamping device until said shaft is positioned at least partially in a groove in a side surface of said radiation treatment block and said oversized end portion of said shaft is positioned above and adjacent to said top surface of said radiation treatment block;

(h) adjusting said nut on said threaded end portion of said rod until said oversized end portion of said shaft engages said top surface of said radiation treatment block or one or more face of said groove and compressibly affixes said radiation treatment block to said upper face of said radiation treatment block mounting plate.

In a twelfth aspect the present invention provides for an adjustable radiation treatment block mounting tray comprising:

(a) a substantially rigid frame body having a top face and a bottom face, an upper frame body member, a lower frame body member, and opposing side frame body members, said frame body having a generally central opening;

(b) a plate having an upper face and a lower face, said lower face of said plate being positioned on said top face of said frame body, said plate having at least one radiation treatment block mounting hole or slot extending through said plate from said upper face to said lower face for use in mounting a radiation treatment block to said upper face of said plate;

(c) means to releasably secure said plate to said frame body, said means allowing said plate to move relative to said frame body when in a released position and when in a fastened position said means compressibly secures said plate to said frame body.

In a thirteenth aspect the present invention provides for an adjustable radiation treatment block mounting tray comprising:

(a) a substantially rigid frame body having a top face and a bottom face, an upper frame body member, a lower frame body member, and opposing side frame body members, said frame body having a generally central opening, and at least one bore for receiving a releasable fastener therein;

(b) a plate having an upper face and a lower face, said lower face of said plate being positioned on said top face of said frame body, said plate having at least one mounting hole or slot extending through said plate from said upper face to said lower face for use in mounting a radiation treatment block to said upper face of said plate, and at least one orifice extending through said plate from said upper face to said lower face, with at least one orifice being positioned over at least one bore in said frame body;

(c) at least one releasable fastener to releasably secure said plate to said frame body, said releasable fastener having a head portion at one end and a shank portion at an opposite end, said shank portion of each releasable fastener being positioned through an orifice in said plate and inserted into a bore in said frame body, wherein a diameter of said orifice is larger than a diameter of said shank portion to allow said plate to move relative to said frame body when said releasable fastener is in a released position, a diameter of said head portion being larger than a diameter of said orifice such that when said releasable fastener is in a fastened position said head portion compressibly secures said plate to said frame body.

In a fourteenth aspect the present invention provides for an adjustable radiation treatment block mounting tray comprising:

(a) a substantially rigid frame body, said frame body having a top face and a bottom face, an upper frame body member, a lower frame body member, and opposing side frame body members, a generally central opening and least one bore for receiving a releasable fastener therein;

(b) a plate having an upper face and a lower face, said lower face of said plate being positioned on said top face of said frame body, said plate having at least one mounting hole or slot extending through said plate from said upper face to said lower face for use in mounting a radiation treatment block to said upper face of said plate and at least one orifice extending through said plate from said upper face to said lower face, with at least one orifice being positioned over at least one bore in said frame body;

(c) at least one releasable fastener to releasably secure said plate to said frame body, said releasable fastener having a head portion at one end, a shank portion at an opposite end and a washer positioned on said shank portion adjoining said head portion, said shank portion of each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said washer being greater than a diameter of said orifice such that when said releasable fastener is in a fastened position said releasable fastener and washer compressibly secure said plate to said frame body.

In a fifteenth aspect the present invention provides for an adjustable radiation treatment block mounting tray comprising:

(a) a substantially rigid frame body, said frame body having a top face and a bottom face, an upper frame body member, a lower frame body member, opposing side frame body members, a generally central opening, and a plurality of bores for receiving a releasable fastener therein;

(b) a plate having an upper face and a lower face, said lower face of said plate being positioned on said top face of said frame body, said plate having at least one mounting hole or slot extending through said plate from said upper face to said lower face for use in mounting a radiation treatment block to said upper face of said plate, and four orifices extending through said plate from said upper face to said lower face, each orifice positioned over a bore in said frame body;

(c) four releasable fasteners to releasably secure said plate to said frame body, each releasable fastener having a head portion at one end, a shank portion at an opposite end and a washer positioned on said shank portion adjoining said head portion, each shank portion of each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said washer being greater than a diameter of said orifice such that when said releasable fastener is in a fastened position, said releasable fasteners and washers compressibly secure said plate to said frame body.

In a sixteenth aspect the present invention provides for an adjustable radiation treatment block mounting tray comprising:

(a) a substantially rigid frame body having a top face and a bottom face, an upper frame body member, a lower frame body member, and opposing side frame body members, said frame body having a generally central opening, and at least one bore for receiving a releasable fastener therein;

(b) a plate having an upper face and a lower face, said bottom face of said frame body being positioned on said upper face of said plate, said plate having at least one mounting hole or slot extending through said plate from said upper face to said lower face for use in mounting a radiation treatment block to said upper face of said plate, and at least one orifice extending through said plate from said upper face to said lower face, with at least one orifice being positioned over at least one bore in said frame body;

(c) at least one releasable fastener to releasably secure said plate to said frame body, said releasable fastener having a head portion at one end and a shank portion at an opposite end, said shank portion of each releasable fastener being positioned through an orifice in said plate and inserted into a bore in said frame body, wherein a diameter of said orifice is larger than a diameter of said shank portion to allow said plate to move relative to said frame body when said releasable fastener is in a released position, a diameter of said head portion being larger than a diameter of said orifice such that when said releasable fastener is in a fastened position said head portion compressibly secures said plate to said frame body.

In a seventeenth aspect the present invention provides for an adjustable radiation treatment block mounting tray comprising:

(a) a substantially rigid frame body, said frame body having a top face and a bottom face, an upper frame body member, a lower frame body member, and opposing side frame body members, a generally central opening and least one bore for receiving a releasable fastener therein;

(b) a plate having an upper face and a lower face, said bottom face of said frame body being positioned on said upper face of said plate, said plate having at least one mounting hole or slot extending through said plate from said upper face to said lower face for use in mounting a radiation treatment block to said upper face of said plate and at least one orifice extending through said plate from said upper face to said lower face, with at least one orifice being positioned over at least one bore in said frame body;

(c) at least one releasable fastener to releasably secure said plate to said frame body, said releasable fastener having a head portion at one end, a shank portion at an opposite end and a washer positioned on said shank portion adjoining said head portion, said shank portion of each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said washer being greater than a diameter of said orifice such that when said releasable fastener is in a fastened position said releasable fastener and washer compressibly secure said plate to said frame body.

In an eighteenth aspect the present invention provides for an adjustable radiation treatment block mounting tray comprising:

(a) a plate having an upper face and a lower face, said plate having at least one mounting hole or slot extending through said plate from said upper face to said lower face for use in mounting a radiation treatment block to said upper face, said plate further having a plurality of bores for receiving a releasable fastener therein;

(b) a substantially rigid frame body having a top face and a bottom face, said bottom face of said frame body being positioned on said upper face of said plate, said frame body having an upper frame body member, a lower frame body member, and opposing side frame body members, said frame body having a generally central opening, said frame body further having at least one orifice extending through said frame body from said top face to said bottom face, at least one orifice being positioned over at least one bore in said plate;

(c) at least one releasable fastener to releasably secure said frame body to said plate, said fastener having a head portion at one end and a shank portion at an opposite end, said shank portion of each releasable fastener being positioned through an orifice in said frame body and inserted into a bore in said plate, a diameter of said orifice being larger than a diameter of said shank portion to allow said frame body to move relative to said plate when said releasable fastener is in a released position, a diameter of said head portion being larger than a diameter of said orifice such that when said releasable fastener is in a fastened position said head portion compressibly secures said frame body to said plate.

In a nineteenth aspect the present invention provides for an adjustable radiation treatment block mounting tray comprising:

(a) a plate having an upper face and a lower face, said plate having at least one mounting hole or slot extending through said plate from said upper face to said lower face for use in mounting a radiation treatment block to said upper face, said plate further having a plurality of bores for receiving a releasable fastener therein;

(b) a substantially rigid frame body having a top face and a bottom face, said bottom face of said frame body being positioned on said upper face of said plate, said frame body having an upper frame body member, a lower frame body member, opposing side frame body members, said frame body having a generally central opening, said frame body further having at least one orifice extending through said frame body from said top face to said bottom face, at least one orifice being positioned such that said orifice is aligned over at least one bore in said plate;

(c) at least one releasable fastener to releasably secure said frame body to said plate, said releasable fastener having a head portion at one end, a shank portion at an opposite end and a washer positioned on said shank portion adjoining said head portion, said shank portion of each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said washer being greater than a diameter of said orifice such that when said releasable fastener is in a fastened position said releasable fastener and washer compressibly secure said frame body to said plate.

In a twentieth aspect the present invention provides for an adjustable radiation treatment block mounting tray comprising:

(a) a substantially rigid frame body, said frame body having a top face and a bottom face, an upper frame body member, a lower frame body member, and opposing side frame body members, said frame body having a generally central opening, said frame body further having a plurality of threaded bores for receiving a threaded rod therein;

(b) a plate having an upper face and a lower face, said lower face of said plate being positioned on said top face of said frame body, said plate having at least one mounting hole or slot extending through said plate from said upper face to said lower face for use in mounting a radiation treatment block to said upper face, said plate further having at least one orifice extending through said plate from said upper face to said lower face, at least one orifice being positioned over at least one threaded bore in said frame body;

(c) at least one rod having opposing end portions, both of said end portions of said rod being threaded, one end portion of said rod being inserted into a threaded bore in said frame body, an opposite exposed end portion of said rod being positioned through an orifice in said plate, a diameter of said rod being less than a diameter of said orifice in said plate, a threaded nut being attached to said exposed end portion of said rod, a diameter of said nut being greater than a diameter of said orifice such that when said nut is in a fastened position said nut compressibly secures said plate to said frame body and when said nut is in a released position allowing said plate to move relative to said frame body.

In a twenty-first aspect the present invention provides for an adjustable radiation treatment block mounting tray comprising:

(a) a substantially rigid frame body, said frame body having a top face and a bottom face, an upper frame body member, a lower frame body member, and opposing side frame body members, said frame body having a generally central opening, said frame body further having a plurality of threaded bores for receiving a threaded rod therein;

(b) a plate having an upper face and a lower face, said lower face of said plate being positioned on said top face of said frame body, said plate having at least one mounting hole or slot extending through said plate from said upper face to said lower face for use in mounting a radiation treatment block to said upper face, said plate further having at least one orifice extending through said plate from said upper face to said lower face, at least one orifice being positioned over at least one threaded bore in said frame body;

(c) at least one rod having opposing end portions, both of said end portions of said rod being threaded, one end portion of said rod being inserted into a threaded bore in said frame body, an opposite exposed end portion of said rod being positioned through an orifice in said plate, a diameter of said rod being less than a diameter of an orifice in said plate, a washer being positioned over said exposed end portion of said rod and positioned on said upper face of said plate, a diameter of said washer being greater than a diameter of said orifice, a nut being attached to said exposed end portion of said rod, such that when said nut is in a fastened position said nut and washer compressibly secure said plate to said frame body and when said nut is in a released position allowing said plate to move relative to said frame body.

In a twenty-second aspect the present invention provides for an adjustable radiation treatment block mounting tray comprising:

(a) a substantially rigid frame body, said frame body having a top face and a bottom face, an upper frame body member, a lower frame body member, and opposing side frame body members, said frame body having a generally central opening, said frame body further having at least one tray adjustment slot extending through said frame body from said top face to said bottom face;

(b) a plate having an upper face and a lower face, said lower face of said plate being positioned on said top face of said frame body, said plate having at least one mounting hole or slot extending through said plate from said upper face to said lower face for use in mounting a radiation treatment block to said upper face, said plate further having at least one tray adjustment slot extending through said plate from said upper face to said lower face, at least one tray adjustment slot in said plate being generally perpendicular to a tray adjustment slot in said frame body and being positioned to overlap a tray adjustment slot in said frame body;

(c) at least one releasable fastener to releasably secure said plate to said frame body, said releasable fastener having a head portion at one end, a shank portion at an opposite end, said shank portion of each releasable fastener positioned through both a tray adjustment slot in said plate and a tray adjustment slot in said frame body wherein when said releasable fastener is in a fastened position said releasable fastener compressibly secures said plate to said frame body and when said releasable fastener is in a released position said releasable fastener allows said plate to move relative to said frame body.

In a twenty-third aspect the present invention provides for a method for adjusting a radiation treatment block in a radiation beam comprising:

(a) providing a radiation treatment block mounted on a plate of an adjustable radiation treatment block mounting tray, said adjustable radiation treatment block mounting tray being installed on a radiation treatment machine, said adjustable treatment block mounting tray comprising:

a substantially rigid frame body having a top face and a bottom face, an upper frame body member, a lower frame body member, and opposing side frame body members, said frame body having a generally central opening;

a plate having an upper face and a lower face, said lower face of said plate being positioned on said top face of said frame body, said plate having at least one mounting hole or slot extending through said plate from said upper face to said lower face for use in mounting a radiation treatment block to said upper face of said plate;

means to releasably secure said plate to said frame body, said means allowing said plate to move relative to said frame body when said means is in a released position and when said means is in a fastened position said means compressibly securing said plate to said frame body;

(b) adjusting said means to a released position so that said plate and said radiation treatment block affixed thereto can move relative to said frame body;

(c) aligning said radiation treatment block within said radiation beam by moving said plate until said radiation treatment block is correctly aligned within said radiation beam for a prescribed treatment of a patient;

(d) adjusting said means to a fastened position compressibly securing said plate to said frame body and securing said radiation treatment block within said radiation beam.

In a twenty-fourth aspect the present invention provides for a method for adjusting a radiation treatment block in a radiation beam comprising:

(a) providing a radiation treatment block mounted on a plate of an adjustable radiation treatment block mounting tray, said adjustable radiation treatment block mounting tray being installed on a radiation treatment machine, said adjustable radiation treatment block mounting tray comprising:

a substantially rigid frame body having a top face and a bottom face, an upper frame body member, a lower frame body member, and opposing side frame body members, said frame body having a generally central opening, said frame body further having at least one bore for receiving a releasable fastener therein;

a plate having an upper face and a lower face, said lower face of said plate being positioned on said top face of said frame body, said plate having at least one mounting hole or slot extending through said plate from said upper face to said lower face for use in mounting a radiation treatment block to said upper face of said plate, said plate further having at least one orifice extending through said plate from said upper face to said lower face, at least one orifice being positioned over at least one bore in said frame body;

at least one releasable fastener to releasably secure said plate to said frame body, at least one releasable fastener having a head portion at one end, a shank portion at an opposite end, said shank portion of said each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said head portion being greater than a diameter of said orifice such that when said releasable fastener is in a fastened position said head portion compressibly secures said plate to said frame body;

(b) adjusting each releasable fastener to a released position so that said plate and said radiation treatment block affixed thereto can move relative to said frame body;

(c) aligning said radiation treatment block within said radiation beam by moving said plate until said radiation treatment block is correctly aligned within said radiation beam for a prescribed treatment of a patient;

(d) adjusting at least one releasable fastener until said releasable fastener is in a fastened position compressibly securing said plate to said frame body and securing said radiation treatment block within said radiation beam.

In a twenty-fifth aspect the present invention provides for a method for adjusting a radiation treatment block in a radiation treatment beam comprising:

(a) providing a radiation treatment block mounted on a plate of an adjustable radiation treatment block mounting tray, said adjustable radiation treatment block mounting tray being installed on a radiation treatment machine, said adjustable radiation treatment block mounting tray comprising:

a substantially rigid frame body having a top face and a bottom face, an upper frame body member, a lower frame body member, and opposing side frame body members, said frame body having a generally central opening, said frame body further having at least one bore for receiving a releasable fastener therein;

a plate having an upper face and a lower face, said lower face being positioned on said top face of said frame body, said plate having at least one mounting hole or slot extending through said plate from said upper face to said lower face for use in mounting a radiation treatment block to said upper face, said plate further having at least one orifice extending through said plate from said upper face to said lower face, at least one orifice being positioned over at least one bore in said frame body;

at least one releasable fastener to releasably secure said plate to said frame body, at least one releasable fastener having a head portion at one end, a shank portion at an opposite end and a washer positioned on said shank portion adjoining said head portion, said shank portion of each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said washer being greater than a diameter of said orifice such that when said releasable fastener is in a fastened position said releasable fastener and washer compressibly secure said plate to said frame body;

(b) adjusting each releasable fastener to a released position so that said plate and radiation treatment block can move relative to said frame body;

(c) aligning said radiation treatment block within said radiation beam by moving said plate until said radiation treatment block is correctly aligned within said radiation beam for a prescribed treatment of a patient;

(d) adjusting at least one releasable fastener until said fastener is in a fastened position compressibly securing said plate to said frame body and securing said radiation treatment block within said radiation beam.

In a twenty-sixth aspect the present invention provides for a template for use with a commercially available foam block cutting machine for making a form to cast a radiation treatment block, comprising a sheet, said sheet having marked or inscribed thereon at least one perimetric outline of a radiation treatment block.

In a twenty-seventh aspect the present invention provides for a template for use with a commercially-available foam block cutting machine for making a form to cast a radiation treatment block, said template comprising a transparent sheet, said sheet having marked or inscribed thereon perimetric outlines of radiation treatment blocks having different sizes, each perimetric outline of a radiation treatment block present on said template having four sides, being rectangular in shape, and having four corners, each of said sides having a rectangular notch positioned thereon, each perimetric outline of a radiation treatment block present on said template having a rectangular notch present on each corner of said perimetric outline, said template further having a horizontal and a vertical line that intersect at a center of said perimetric outlines of said template, said template further having a radiation treatment block alignment line marked or scribed thereon, said radiation treatment block alignment line being positioned such that it intersects with one side of each perimetric outline of a radiation treatment block present on said template, said side having a protrusion thereon extending from said side at the intersection of said side with the radiation treatment block alignment line.

In a twenty-eighth aspect the present invention provides for a method for making a foam form to cast a radiation treatment block comprising:
(e) providing a commercially-available foam block cutting machine for making a form to cast a radiation treatment block, said foam block cutting machine having a light table, a hot wire frame, said hot wire frame having an upper hot wire frame member and a lower hot wire frame member, and a hot wire for cutting a foam block, said hot wire being positioned between said upper and lower hot wire frame members, said foam block cutting machine further having a stylus connected to said hot wire frame for tracing a perimetric outline of a radiation treatment block, and a tray for holding a foam block;
(f) positioning a template for use with a foam block cutting machine for making a form to cast a radiation treatment block on said light table, said template comprising a transparent sheet, said sheet having marked or inscribed thereon a perimetric outline of at least one radiation treatment block;
(g) placing a foam block for casting a radiation treatment block on said tray;
(h) tracing a perimetric outline of a radiation treatment block present on said template with said stylus causing said hot wire to cut said foam block in a same perimetric dimension as said perimetric outline of said radiation treatment block on said template.

In a twenty-ninth aspect the present invention provides for a ruler for use with a template for use with a commercially available foam block cutting machine for making a form to cast a radiation treatment block, said ruler having an elongated rectangular shape, said ruler having four sides, two of said sides being elongated, at least one elongated side having a tab protruding from an elongated side.

In a thirtieth aspect the present invention provides for a ruler for use with a template for use with a commercially available foam block cutting machine for making a form to cast a radiation treatment block, said ruler having four sides, two of said sides being elongated, at least one elongated side having a notch present therein.

Figure 2:
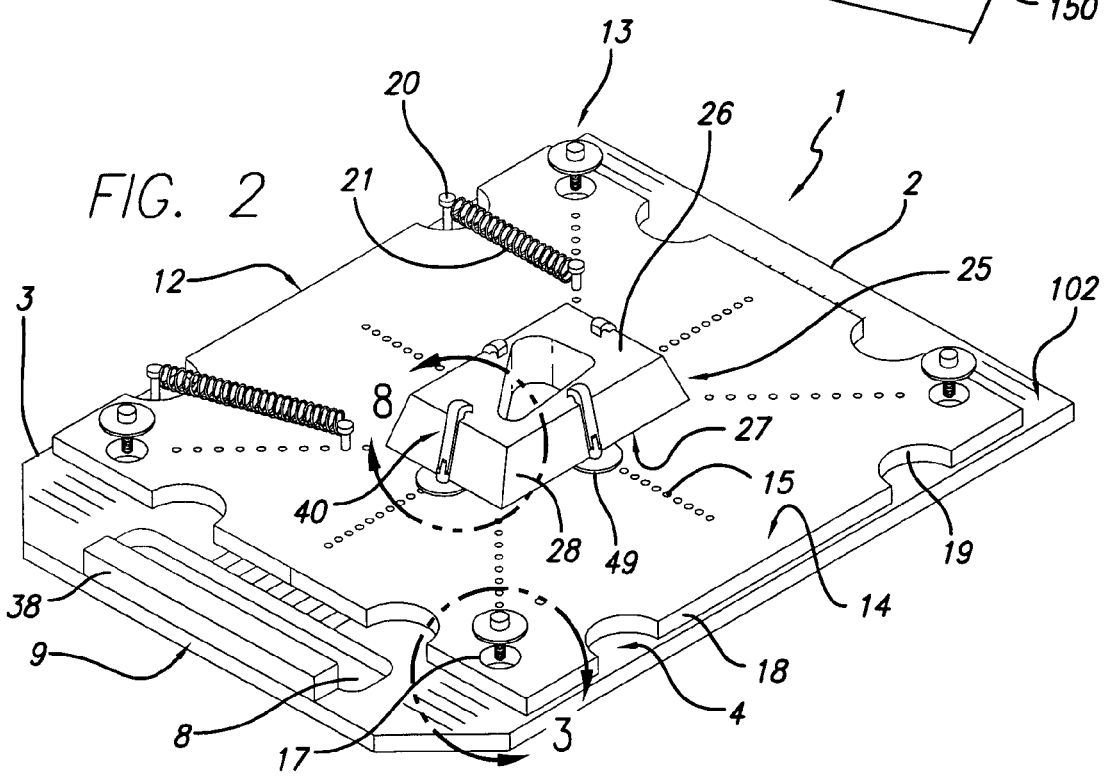
FIG. 2 is an exploded view of a preferred embodiment of the tray of the current invention with a block fixed to it.

FIGS. 1 and 2 generally show a radiation treatment block affixed to an adjustable radiation block mounting tray, however, specific elements present in the adjustable radiation block mounting trays and radiation treatment blocks may best be observed by reference to FIGS. 1–14 in total.

FIG. 1 shows an adjustable radiation block mounting tray 1 ("tray") with a radiation treatment block 25 ("block") affixed to a plate 12. The plate 12 is releasably secured to a frame body 2 by at least one releasable fastener 13. In the embodiment shown, the releasable fasteners 13 are knurled head screws. It is recognized by those skilled in the art that other releasable fasteners, including but not limited to thumb screws, knob screws, adjustable diameter pins, cam clamps, bolts, and screws are equally suitable.

The plate 12 has an upper face 14 and a lower face 101 (shown in FIG. 6). The block 25 is affixed to an upper face 14 of the plate 12 by a plurality of external clamping devices 40 inserted through block mounting holes 15 in the plate 12. It is recognized by those skilled in the art that external clamping devices 40 other than the embodiments shown in the drawings are suitable, including but not limited to clamps, pivot clamps, hook clamps, toggle clamps, swing clamps and nylon ties.

The adjustable radiation block mounting tray 1 can be inserted into guide channels 100 present on a radiation machine 150. With the adjustable radiation block mounting tray 1 positioned in the guide channels 100, the position of the block 25 within a radiation beam 90 can be aligned by adjusting the releasable fasteners 13 to a released position until the plate 12 can move relative to the frame body 2. This allows the block 25 to be easily and precisely aligned so that the radiation beam 90 is correctly and accurately applied to a patient 200. The releasable fasteners 13 can then be adjusted to a fastened position thereby securing the radiation block 25 in the correct alignment.

Figure 7:
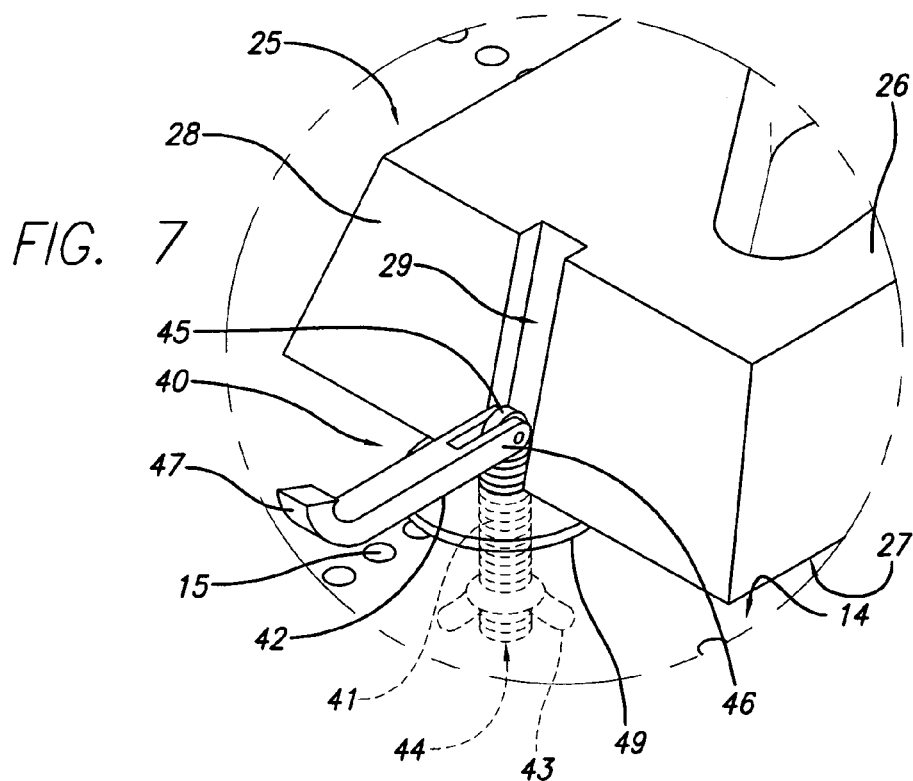
FIG. 7 is a partial view of a preferred embodiment of an external clamping device positioned adjacent to a groove in a side surface present in a radiation block.
Figure 8:
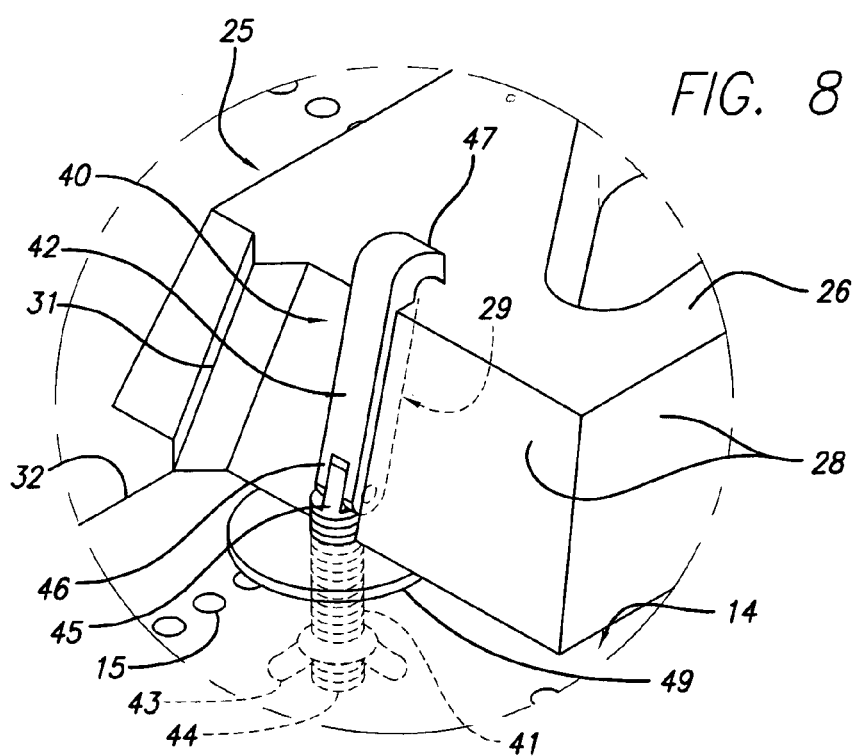
FIG. 8 is a partial view of a preferred embodiment of an external clamping device compressibly securing a radiation treatment block to a plate.

FIG. 2 shows an adjustable radiation treatment block mounting tray 1 having a radiation treatment block 25 mounted on an upper face 14 of the plate 12. The block 25 is compressibly secured to the upper face 14 of the plate 12 of the adjustable radiation block mounting tray 1 using a plurality of external clamping devices 40. The threaded end portion 44 of the rod 41 that is present on the external clamping device 40 can be inserted through a block mounting hole 15 or slot 16 positioned proximate a groove 29 (shown in FIG. 7) in a side surface 28 of the block 25, and a threaded nut 43 can be attached to the threaded end portion 44 of the rod 41 (see FIGS. 7, 8 and 11). An opposite hingeable connection end portion 45 of the rod 41 is hingeably connected to the hingeable connection end portion 46 of the shaft 42 present on the clamping device 40 (see FIGS. 7, 8). The shaft 42 is pivoted until an opposite substantially hook shaped end portion 47 present on the shaft 42 is positioned above a top surface 26 of the radiation treatment block 25 and the shaft 42 is at least partially in the groove 29 (FIGS. 7 & 8). The threaded nut 43 present on the threaded end 44 portion of the rod 41 of the clamping device 40 can be adjusted so that at least part of the substantially hook shaped end portion 47 of the shaft 42 engages the top surface 26 of the block 25 to compressibly secure the block 25 to the upper face 14 of the plate 12 (shown in FIGS. 7 & 8).

The lower face 101 (shown in FIG. 6) of the plate 12 is positioned on a top face 102 (shown in FIG. 6) of the substantially rigid frame body 2. The frame body 2 has one or more bores 6 (see FIG. 10) to receive a releasable fastener 13 therein. A releasable fastener 13 is positioned through at least one orifice 17 present in the plate 12 and inserted into a bore 6. The releasable fastener 13 can be adjusted to a fastened position until the plate 12 is compressibly secured to the frame body 2. The releasable fastener 13 can be adjusted to a released position to allow the plate 12 to be moved relative to the frame body 2. This allows a radiation technologist to adjust and align the position of a radiation treatment block 25 for use in a radiation beam 90 by moving the plate 12 relative to the frame body 2. Once the correct alignment of the block 25 is achieved within the radiation beam 90, the releasable fasteners 13 can be adjusted to a fastened position to compressibly secure the plate 12 to the frame body 2 and fix the block 25 in a correct position. The bores 6 can either be threaded or non-threaded, but are preferably threaded.

In the embodiment shown in FIG. 2 a side frame body member 5 has a slotted orifice 8 that forms a handle portion 9 in a side frame body member 5. A handle fitting 38 can optionally be affixed to the handle portion 9.

In the embodiment shown in FIG. 2, a compressible washer 49 is positioned on the threaded end portion 44 of the rod 41 and is positioned at least partially between the upper face 14 of the plate 12 and the bottom surface 27 of the block 25.

In the embodiment shown, the adjustable radiation block mounting tray 1 has one or more spring mounting fitting 20 affixed to both a top face 102 of an upper frame body member 3 and to the upper face 14 of the plate 12. The plate 12 has notches 19 that extend from an outer edge 18 of the plate 12 into the plate 12. The notches 19 are positioned to align over a spring attachment fitting 20 affixed to a top face 102 of an upper frame body member 3. A spring mounting fitting 20 affixed to a top face 102 of an upper frame body member 3 is connected to a spring attachment fitting 20 affixed to the upper face 14 of the plate 12 by a spring 21. The spring 21 absorbs some of the weight of the block 25 when the adjustable radiation treatment block mounting tray 1 is installed in a radiation treatment machine 150 (shown in FIG. 1) and the releasable fasteners 13 are in a released position. This allows a radiation technologist to more easily move the plate 12 relative to the frame body 2 and align the position of the block 25. It is recognized by those skilled in the art that various types of springs 21 are suitable, for this purpose, including but not limited to coiled springs and elastomeric bands or strips.

Although the embodiment in FIG. 2 shows that the lower face 101 of the plate 12 is positioned on a top face 102 of a substantially rigid frame body 2, other embodiments of the invention are also suitable. In an alternative embodiment, the bottom face 103 (bottom face shown in FIG. 6) of the frame body 2 can be positioned on the upper face 14 of the plate 12.

In another alternative embodiment of an adjustable radiation treatment block mounting tray 1, not shown in a drawing, the adjustable radiation treatment block mounting tray 1 comprises a plate 12 that has an upper face 14 and a lower face 101. The plate has a plurality of bores 6 present therein receiving a releasable fastener 13. The plate 12 further has at least one mounting hole 15 or slot 16 extending through the plate 12 from the upper face 14 to the lower face 101. The adjustable radiation treatment block mounting tray 1 further comprises a substantially rigid frame body 2 having a top face 102 and a bottom face 103. The frame body 2 has at least one orifice 17 extending through the frame body 2. The bottom face 103 of the frame body 2 can be positioned on the upper face 14 of the plate 12 such that at least one orifice 17 in the frame body 2 is positioned over at least one bore 6 in the plate 12. The adjustable radiation treatment block mounting tray 1 further comprises at least one releasable fastener 13 to releasably secure the frame body 2 to the plate. A shank portion 75 of a releasable fastener 13 is positioned through an orifice 17 in the frame body 2 and is inserted in a bore 6 in the plate 12. A diameter of the orifice 17 is larger than a diameter of the shank portion 75 so the plate 12 can move relative to the frame body 2 when the releasable fasteners 13 are in a released position to allow a radiation block 25 affixed to the upper face 14 of the plate 12 to be adjusted in a radiation beam 90. The head portion 76 of the releasable fastener 13 has a diameter larger than a diameter of the orifice 17 such that when a releasable fastener 13 is in a fastened position the head portion 76 compressibly secures the frame body 2 to the plate 12. A releasable fastener 13 can alternatively be provided that has a head portion 76 with a diameter less than a diameter of the orifice 17. In that case a rigid washer 65 with a hole present therein, and that has a diameter greater than an orifice 17 can be positioned on the shank portion 75 adjoining the head portion 76 of the releasable fastener 13. When the releasable fastener 13 is in a fastened position the rigid washer 65 engages the top face 102 of the frame body 2 and the rigid washer 65 and the releasable fastener 13 compressibly secure the frame body 2 to the plate 12.

Although FIG. 2 shows a radiation treatment block 25 affixed to a plate 12 of an adjustable radiation treatment block mounting tray 1 it is recognized that the methods for mounting radiation treatment blocks on a radiation treatment block mounting plate of this invention can also be used to affix a radiation treatment block 25 on a commercially available radiation treatment block mounting plate or tray.

Figure 3:
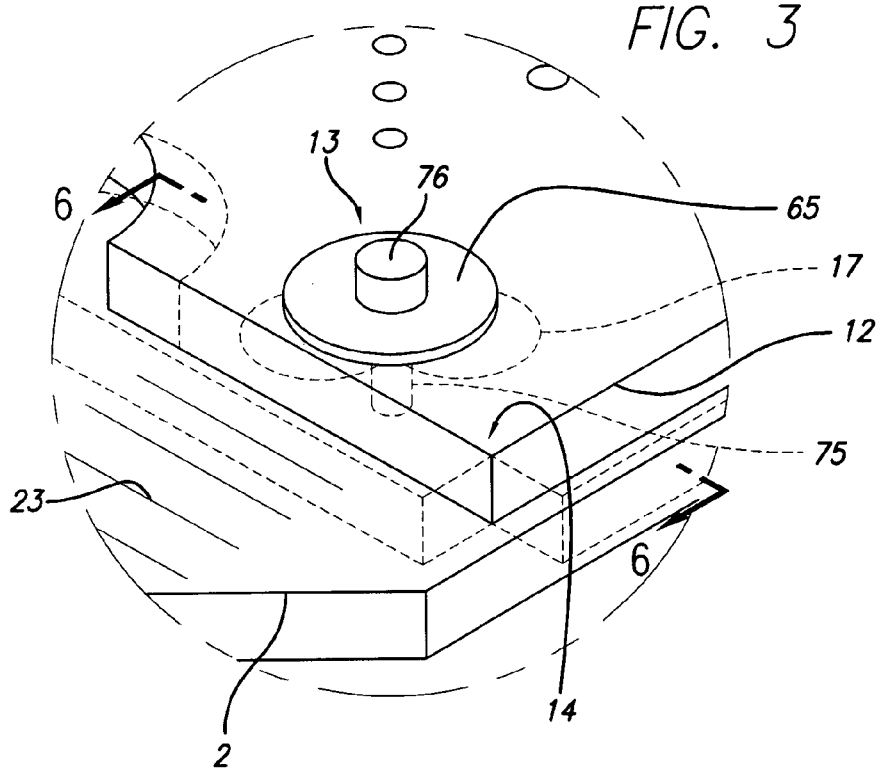
FIG. 3 is a partial view of the tray illustrated in FIG. 2 showing the range of movement of a plate over the surface of the frame.

FIG. 3 shows a range of movement of the plate 12 relative to the frame body 2. A shank portion 75 of a releasable fastener 13 is positioned through a rigid washer 65 and an orifice 17 present in the plate 12 and is inserted into a bore 6 in the frame body 2. In the embodiment shown a shank portion 75 of a releasable fastener 13 and the bore 6 are threaded. However, it is recognized by those skilled in the art, that depending on the releasable fastener 13 selected, a shank portion 75 and a bore 6 do not have to be threaded. The rigid washer 65 is positioned between the upper face 14 of the plate 12 and a head portion 76 of the releasable fastener 13. When the releasable fastener 13 is in a released position, the plate 12 can move relative to the frame body 2 within a range determined by the dimensions of the orifice 17, which can be varied in a manner known by those of skill in the art.

In the embodiment shown, a plurality of measuring gauges 23 are marked or scribed on the frame body 2. The measuring gauges 23 allow a technologist to observably measure the amount of movement that occurs between the plate 12 and the frame body 2 when the position of a block 25 is being adjusted.

Figure 4:
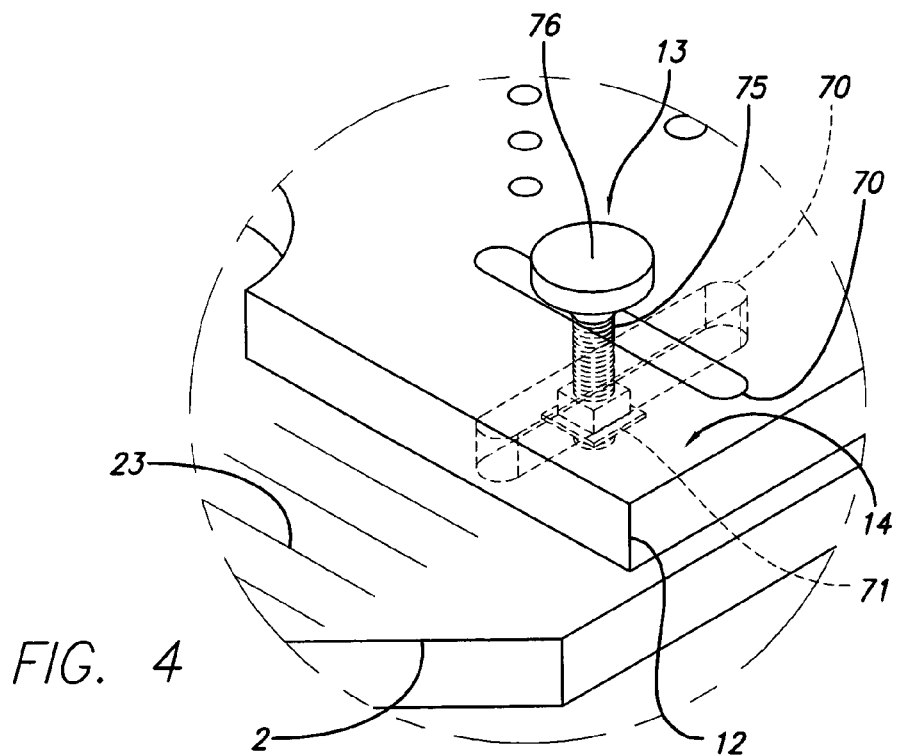
FIG. 4 is a partial view of an embodiment of a tray of the current invention showing a releasable fastener which secures a plate to the frame body of the tray.

FIG. 4 shows an alternative embodiment of the adjustable radiation block mounting tray 1. The plate 12 preferably has at least one tray adjustment slot 70 that is positioned to overlap a tray adjustment slot 70 present in the frame body 2. The tray adjustment slot 70 present in the plate 12 is generally perpendicular to the tray adjustment slot 70 present in the frame body 2. A shank portion 75 present in a releasable fastener 13 is positioned through the tray adjustment slots 70 present in the plate 12 and the frame body 2. In the embodiment, shown the releasable fastener 13 is a knob screw and the shank portion 75 is threaded. A threaded nut 71 can be affixed to the shank portion 75 of the releasable fastener 13. In the embodiment shown, the threaded nut 71 is a T-nut, however, it is recognized by those skilled in the art that other types of nuts are equally suitable for this purpose, including but not limited to a wing nut, a lock nut, a finger nut, a knurled nut, a handle nut or a push nut. It is also recognized that other types of releasable fasteners 13 are suitable, including but not limited to a thumb screw, a knurled head screw, a bolt, a screw and an adjustable diameter pin.

The head portion 76 present in the releasable fastener 13 can be adjusted to a fastened position to compressibly secure the plate 12 to the frame body 2. In an alternative embodiment a rigid washer 65 can be positioned between the head portion 76 of the releasable fastener 13 and the upper face 14 of the plate 12.

FIG. 5 shows a cam clamp 80 as an alternative embodiment of a releasable fastener 13 to releasably secure the plate 12 to the frame body 2. In the embodiment shown, the shank portion 82 of the cam clamp 80 is positioned through a rigid washer 65 having a diameter larger than the orifice 17 that is present in the plate 12 and is inserted into a bore 6 (shown in FIG. 10) present in the frame body 2. In the embodiment shown the shank portion 82 of the cam clamp 80 is threaded and the bore 6 is threaded. The rigid washer 65 is positioned between the cam clamp handle 83 and the upper face 14 of the plate 12. The cam clamp handle 83 is shown in the fastened position. In the fastened position, the cam clamp 80 compressibly secures the rigid washer 65 to the upper face 14 of the plate 12, and the plate 12 to the frame body 2. In the released position, the cam clamp 80 allows the plate 12 to move relative to the frame body 2 so that a radiation treatment block 25 can be properly aligned in the radiation beam 90 (see FIG. 1). It is recognized that a cam clamp 80 can also be used without a rigid washer 65.

FIG. 6 shows a releasable fastener 13 as a means to releasably secure the plate 12 to the frame body 2. A lower face 101 of the plate 12 is positioned on a top face 102 of the frame body 2. A shank portion 75 present in the releasable fastener 13 is inserted through a rigid washer 65 having a diameter larger than an orifice 17 that is present in the plate 12. The rigid washer 65 is positioned between an upper face 14 of the plate 12 and a head portion 76 of a releasable fastener 13. The shank portion 75 of the releasable fastener 13 is positioned through an orifice 17 present in the plate 12 and is inserted into a threaded bore 6 present in the frame body 2. The releasable fastener 13 can be adjusted until the head portion 76 of the releasable fastener 13 engages the rigid washer 65 and compressibly secures the plate 12 to the frame body 2. In the embodiment shown, the releasable fastener 13 is a knurled head screw which is used to releasably secure the plate 12 to frame body 2, however, it is recognized by those skilled in the art that other types of releasable fasteners 13 can be used. It is recognized that a diameter of the head portion 76 of the releasable fastener 13 can be larger than a diameter of an orifice 17 in which case a rigid washer 65 can, optionally, be omitted.

FIG. 7 shows an external clamping device 40 positioned proximate to a groove 29 present in a side surface 28 of a radiation treatment block 25. In the embodiment shown, the external clamping device 40 is comprised of a rod 41, a shaft 42, and a threaded nut 43. The rod 41 has a threaded end portion 44 and an opposite hingeable connection end portion 45. The shaft 42 has a hingeable connection end portion 46 and an opposite substantially hook shaped end portion 47. The hingeable connection end portion 45 of the rod 41 is hingeably connected to the hingeable connection end portion 46 of the shaft 42. The threaded end portion 44 of the rod 41 is inserted through a mounting hole 15 or slot 16 present in the plate 12 positioned proximate to a side surface 28 of the block 25. The threaded nut 43 is attached to the threaded end portion 44 of the rod 41. The shaft 42 is sized and shaped so that it fits at least partially into a groove 29 present in a side surface 28 of a radiation treatment block 25. The groove 29 extends from the top surface 26 to the bottom surface 27 of the radiation treatment block 25 and projects from a side surface 28 into the radiation treatment block 25. In one embodiment, the threaded nut 43 is a wing nut, however, it is recognized by those of skill in the art that other types of nuts including but not limited to a lock nut, a finger nut, a knurled nut, a handle nut and a push nut can be utilized.

In one embodiment, the threaded end portion 44 of the rod 41 is inserted through a compressible washer 49 and the compressible washer 49 is positioned at least partially between the bottom surface 27 of the radiation treatment block 25 and the upper face 14 of the plate 12. It is recognized that the compressible washer 49 does not need to be positioned on the threaded end portion 44 of the rod 41. It is also recognized that one or more compressible washer 49 can be placed between the bottom surface 27 of the radiation treatment block 25 and the upper face 14 of the plate 12. In the preferred embodiment, the compressible washer 49 is made from an elastomeric material such as rubber; however other materials, such as plastic, wood, leather are equally suitable as known by those skilled in the art. It is also recognized by those skilled in the art that alternatively, one or more pieces of compressible material can be positioned between the bottom surface 27 of the radiation treatment block 25 and the upper face 14 of the plate 12.

In the embodiment shown, the shaft 42 is rectangular in shape. However, it is recognized the other shapes are equally suitable, including but not limited to a round or triangular shaft.

The groove 29 in the embodiment shown is rectangular in shape, however it is recognized that other shapes of grooves are equally suitable including but not limited to U-shaped or V-shaped grooves.

It is recognized that in other embodiments of the clamping device 40 of the present invention, the end portion of the shaft 42 opposite the hingeable connection end portion 46 of the shaft 42 does not have to be substantially hook shaped but can be sized and shaped to engage the top surface 26 of the radiation treatment block 25. It is also recognized that in an alternative embodiment of the clamping device 40 of the present invention, the end portion of the shaft 42 opposite the hingeable connection end portion 46 of the shaft 42 can be oversized such that one or more dimension of the opposite end portion of this shaft 42 is greater than one or more dimension of a groove 29 present in a side surface 28 of a radiation treatment block 25. The opposite oversized end portion of the shaft 42 can be positioned over and adjacent to the top surface 26 of the radiation treatment block 25. The threaded nut 43 can be adjusted until the opposite oversized end portion of the shaft 42 engages the top surface 26 of the radiation treatment block 25 or one or more face of the groove 29 and compressibly secures the radiation treatment block 25 to the upper face 14 of the plate 12.

FIG. 8 shows the external clamping device 40 (shown in FIG. 7) after the shaft 42 has been pivoted so that the substantially hook shaped end portion 47 of the shaft 42 is positioned above and adjacent to the top surface 26 of the block 25 and at least part of the shaft 42 is present within the groove 29 in a side surface 28 of the block 25. The threaded nut 43 can be adjusted until at least part of the substantially hook shaped end portion 47 of the shaft 42 engages the top surface 26 of the block 25 and compressibly secures the block 25 to the upper face 14 of the plate 12.

FIG. 8 further shows an alternative embodiment of a radiation treatment block 25. In the embodiment shown, the radiation treatment block 25 further comprises a ridge 31 protruding from a side surface 28 of a radiation treatment block 25. The ridge 31 extends from the top surface 26 to the bottom surface 27 of a radiation treatment block 25. The ridge 31 can be positioned on a side surface 28 of a radiation treatment block 25 so that it is aligned over a radiation treatment block alignment line 32 that is marked or scribed on an upper face 14 of a plate 12 of an adjustable radiation treatment block mounting tray 1. The ridge 31 and the radiation treatment block alignment line 32 can assist a radiation technologist to correctly position and orient a radiation treatment block 25 on the plate 12.

FIG. 9 shows an alternative embodiment of a clamping device 40 and a radiation treatment block 25. The rod 41 has a threaded end portion 44 and at its opposite end a hingeable connection end portion 45. The shaft 42 has a hingeable connection end portion 46 and at its opposite end a substantially hook shaped end portion 47. The hingeable connection end portion 45 of the rod 41 and the hingeable connection end portion 46 of the shaft 42 are hingeably connected. The radiation treatment block 25 has a groove 29 located at at least one corner edge 30, said corner edge 30 formed by the intersection of two side surfaces 28. The groove 29 extends from the top surface 26 to the bottom surface 27 of the radiation treatment block 25 and projects from the corner edge 30 inward into the radiation treatment block 25. In the embodiment shown, the threaded end portion 44 of the rod 41 can be inserted through a compressible washer 49 and the compressible washer 49 is positioned at least partially between the bottom surface 27 of the radiation treatment block 25 and the upper face 14 of the plate 12. In the embodiment shown, the threaded end portion 44 of the rod 41 is inserted in a mounting hole 15 or slot 16 positioned proximate to a groove 29 in a corner edge 30 of radiation treatment block 25. A threaded nut 43 is attached to the threaded end portion 44 of the rod 41. The shaft 42 is pivoted until the substantially hook shaped end portion 47 of the shaft 42 is positioned above and adjacent to the top surface 26 of the radiation treatment block 25 and at least part of the shaft 42 is positioned within the groove 29 in the radiation treatment block 25. The threaded nut 43 can be adjusted until at least part of the substantially hook shaped end portion 47 of the shaft 42 engages the top surface 26 of the radiation treatment block 25 and compressibly secures the radiation treatment block 25 to the upper face 14 of the plate 12.

The clamping device 40 shown in FIG. 9 can also be used to affix a radiation treatment block 25 without a groove 29 to the upper face 14 of the plate 12. The threaded end portion 44 of the rod 41 can be inserted in a mounting hole 15 or slot 16 positioned proximate to at least one side surface 28 of a radiation treatment bock 25. A threaded nut 43 can be attached to the threaded end portion 44 of the rod 41. The shaft 42 can be pivoted until the substantially hook shaped end portion 47 is positioned above and adjacent to the top surface 26 of the radiation treatment block 25. The threaded nut 43 can then be adjusted on the threaded end portion 44 until at least part of the substantially hook shaped end portion 47 engages the top surface 26 of the radiation treatment block 25 and compressibly secures the radiation treatment block 25 to the upper face 14 of the plate 12.

Figure 10:
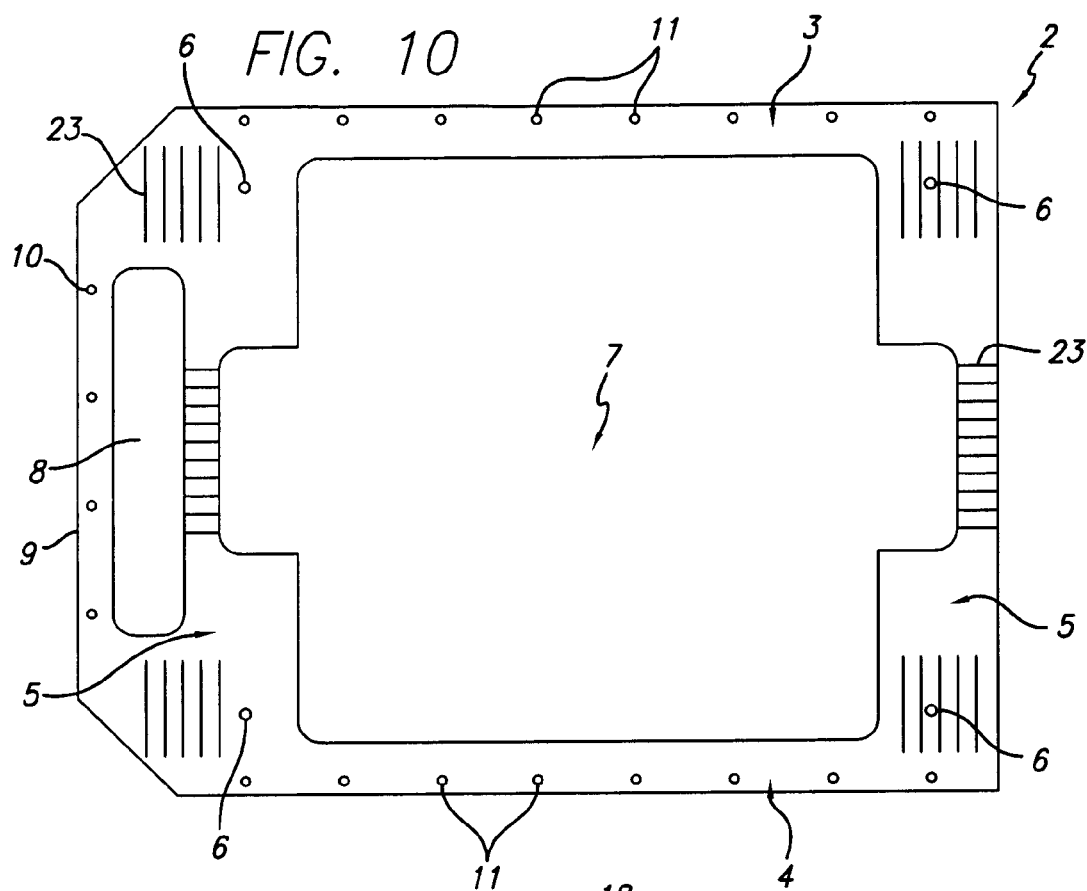
FIG. 10 is a plan view of the frame body of an adjustable radiation block mounting tray.

FIG. 10 shows the substantially rigid frame body 2. The frame body 2 has an upper frame body member 3, a lower body frame member 4, and opposing side frame body members 5. The frame body 2 has a generally central opening 7. In the embodiment shown, at least one side frame body member 5 has a slotted orifice 8 that forms a handle portion 9 in a side frame body member 5. It is recognized that the frame body 2 can be fabricated without a slotted orifice 8 and a handle portion 9. In the embodiment shown, a plurality of holes 10 are provided in the handle portion 9 to mount handle fitting 38 (shown in FIGS. 1 and 2).

The frame body 2 also has a plurality of bores 6 for receiving a releasable fastener therein for compressibly securing the plate 12 to the frame body 2. A plurality of rail mounting bores 11 are also provided in the upper and lower frame body members 3, 4. In one embodiment, the rail mounting bores 11 can be used to affix a spring attachment fitting 20 (shown in FIG. 2) to the upper frame body member 3.

In the embodiment shown, a plurality of measuring gauges 23 are marked or scribed on the frame body 2. The gauges 23 allow a radiation technologist to observably measure the amount of movement between the plate 12 and the frame body 2 when the position of a block 25 is being adjusted. It is also recognized that optionally one or more measuring gauge 23 can be marked or scribed on the plate 12.

In the embodiment shown, the frame body 2 is fabricated from metal, however, it is recognized by those skilled in the art that other materials, for example, plastic, fiberglass, wood, carbon fiber, graphite or composites are also suitable.

Figure 11:
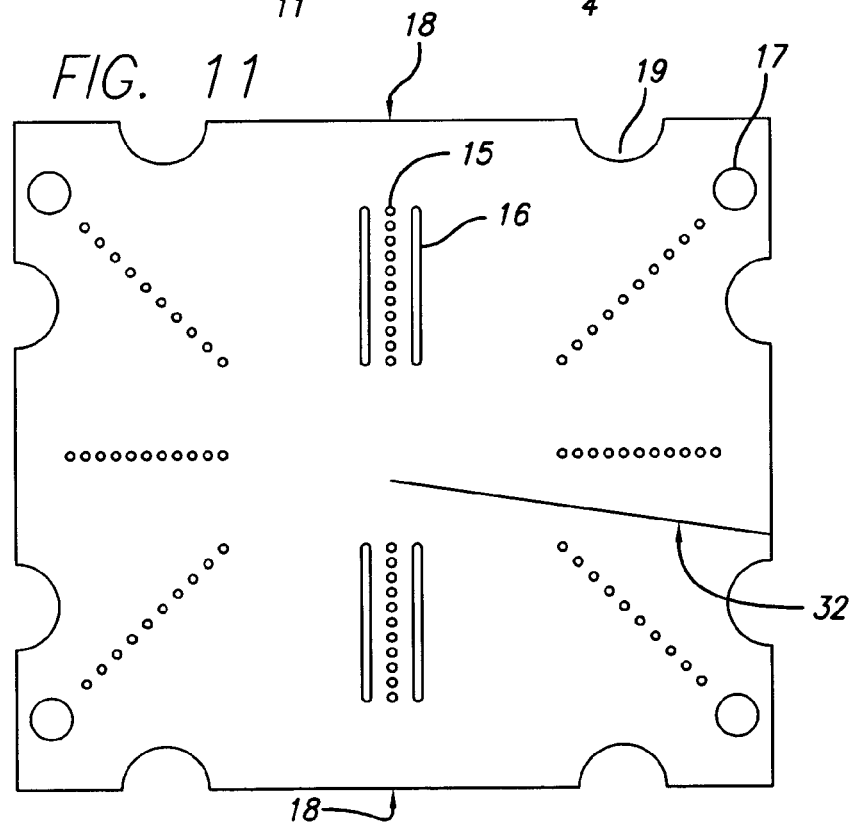
FIG. 11 is a plan view of a plate of an adjustable radiation block mounting tray.

FIG. 11 shows a plate 12 of an adjustable radiation block mounting tray 1. The plate 12 has a plurality of mounting holes 15 and slots 16 for receiving clamping means to affix a radiation treatment block 25 to said plate 12, said mounting holes and slots extending through said plate from said upper face 14 to said lower face 101 the holes and slots can be positioned to allow radiation treatment block 25 having different sizes to be affixed to the plate 12. In the embodiment shown, the plate 12 has both mounting holes 15 and slots 16, however the plate can also be fabricated with one or more mounting hole 15 or one or more mounting slot 16. Although it is preferable that the mounting holes 15 or slots 16 extend through the plate 12, in an alternative embodiment the mounting holes 15 or slots 16 can extend only partially through the plate 12 from the upper face 14 depending on the means selected to affix a radiation treatment block 25 to a radiation treatment block mounting plate 12. The plate 12 also has a plurality of orifices 17 extending through the plate 12 from the upper face 14 to the lower face 101 (shown in FIG. 6), said orifices 17 are positioned so that at least one orifice 17 is aligned over a bore 6 in the frame body 2 for receiving a releasable fastener 13 when the lower face 101 of plate 12 is positioned on the top face 102 of the frame body 2. In the embodiment shown, the plate 12 has a plurality of notches 19 extending from an outer edge 18 of the plate 12 into the plate 12. In the embodiment shown, the notches 19 are semi-circular, however, notches of other shapes, such as rectangular and triangular are also suitable. The notches 19 in the plate 12 are sized and positioned so that when the lower face 101 of the plate 12 is positioned on the top face 102 of the frame body 2 the notches 19 can be aligned over spring attachment fittings 20 affixed to the upper frame body member 3 and allow the plate 12 to move relative to the frame body 2 when the releasable fasteners 13 are in a released position.

In the embodiment shown, the plate 12 is made from polycarbonate, however, other material such as acrylic, plastics, composites and perforated metal are also suitable.

FIG. 11 also shows an optional radiation treatment block alignment line 32 scribed or marked on an upper face 14 of the plate 12. The radiation treatment block alignment line 32 is positioned such that a ridge 31 positioned on a side surface 28 of radiation treatment blocks 25 having different sizes will be positioned over the radiation treatment block alignment line 32 when the radiation treatment blocks 25 are affixed on the upper face 14 of the plate 12.

Figure 12:
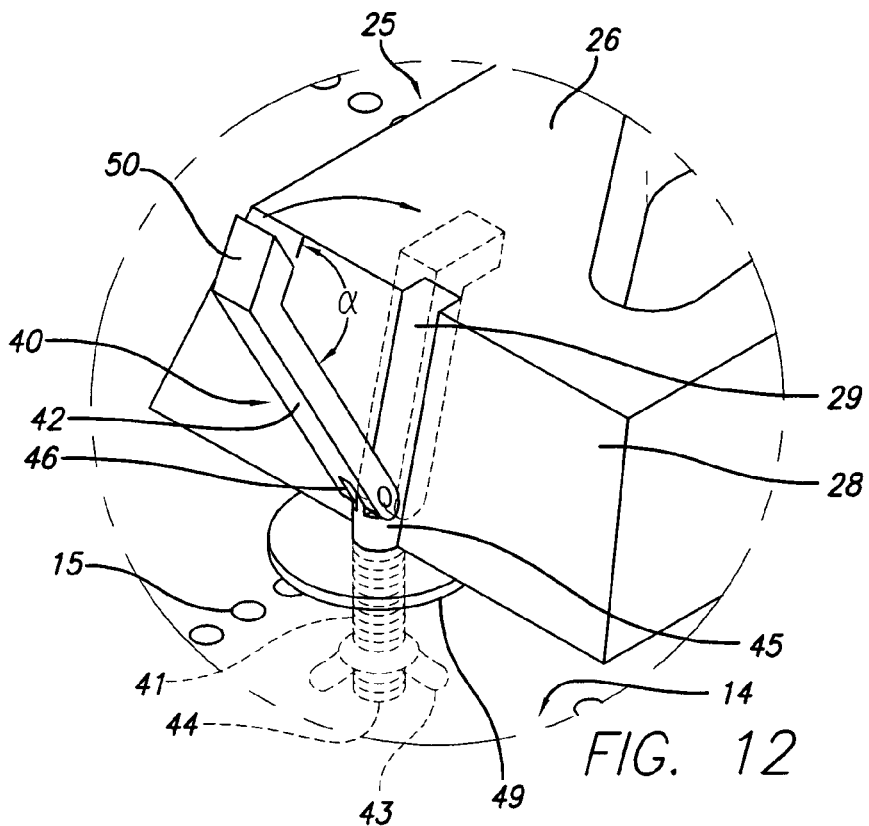
FIG. 12 shows an alternative embodiment of a clamping device having a substantially lever shaped end portion of its shaft.

FIG. 12 shows an alternative embodiment of a clamping device 40. The embodiment of the clamping device 40 shown is comprised of a rod 41, a shaft 42 and a threaded nut 43. The rod 41 has a threaded end portion 44 and at its opposite end, a hingeable connection end portion 45. The shaft 42 has a hingeable connection end portion 46 and at its opposite end, a substantially lever shaped end portion 50. The substantially lever shaped end portion 50 and the shaft 42 forming an angle α, which is between about 60 and about 120 degrees, and is preferably about 90 degrees. The hingeable connection end portion 45 of the rod 41 hingeably connects to the hingeable connection end portion 46 of the shaft 42. The threaded end portion 44 of the rod 41 can be inserted in a mounting hole 15 or slot 16 (shown in FIG. 11) present in the plate 12 that is located proximate to a groove 29 that is present in a side surface 28 of the radiation treatment block 25. A threaded nut 43 can be positioned on the threaded end portion 44 of the rod 41. The shaft 42 can be pivoted until the substantially lever shaped end portion 50 is positioned above the top surface 26 of the block 25 and the shaft 42 is at least partially within the groove 29. The threaded nut 43 can be adjusted on the threaded end portion 44 of the rod 41 so that at least part of the substantially lever shaped end portion 50 engages the top surface 26 of the radiation treatment block 25 and compressibly secures the radiation treatment block 25 to the upper face 14 of the plate 12.

In the embodiment shown, at least one side surface 28 of a radiation treatment block 25 has groove 29 present therein, however, it is recognized that the clamping device 40 shown in FIG. 12 can be used to affix a radiation treatment block 25 without a groove 29 present therein, to an upper face 14 of a plate 12. The threaded end portion 44 of the rod 41 can be inserted in a mounting hole 15 or a slot 16 positioned proximate at least one side surface 28 of a radiation treatment block 25. A threaded nut 43 can be attached to the threaded end portion 44 of the rod 41. The shaft 42 can be pivoted until the substantially lever shaped end portion 50 is positioned above and adjacent to the top surface 26 of the radiation treatment block 25. The threaded nut 43 can be adjusted on the threaded end portion 44 until at least part of the substantially lever shaped end portion 50 engages the top surface 26 of the radiation treatment block 25 and compressibly secures the radiation treatment block 25 to the upper face 14 of the plate 12.

In the embodiment shown, a compressible washer 49 is positioned on the rod 41 and is located at least partially between the upper face 14 and the bottom surface 27 of the radiation treatment block 25.

Figure 13:
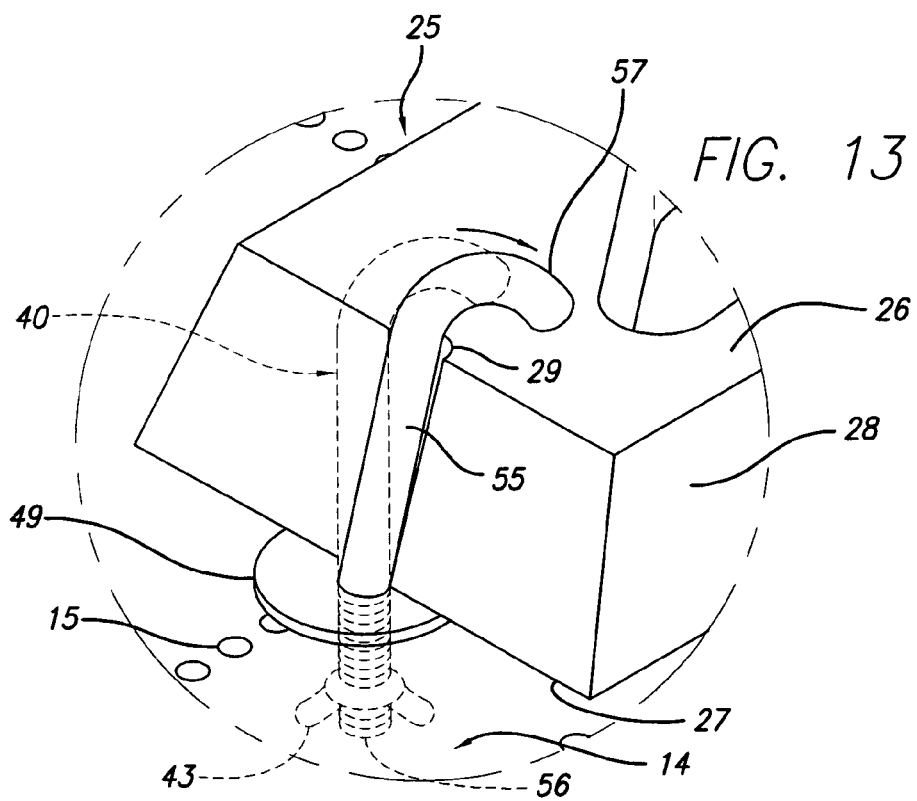
FIG. 13 shows an alternative embodiment of a clamping device having a flexible shaft.

FIG. 13 shows an alternative embodiment of a clamping device 40. The embodiment of the clamping device 40 shown is comprised of a flexible shaft 55 and a threaded nut 43. The flexible shaft 55 has a threaded end portion 56 and at an opposite end, an end portion sized and shaped to engage the top surface 26 of the radiation treatment block 25. In the embodiment shown in FIG. 13 the opposite end portion of the flexible shaft 55 is a substantially hook shaped end portion 57. The threaded end portion 56 can be inserted in a mounting hole 15 or slot 16 (shown in FIG. 11) in the plate 12 that is located proximate to a groove 29 present in a side surface 28 of a block 25. A threaded nut 43 can be positioned on the threaded end portion 56 of the flexible shaft 55. The flexible shaft 55 can be flexed so that the substantially hook shaped end portion 57 of the flexible shaft 55 is positioned above the top surface 26 of the block 25 and the flexible shaft 55 is at least partially within a groove 29. The threaded nut 43 can be adjusted on the threaded end portion 56 of the flexible shaft 55 so that the substantially hook shaped end portion 57 of the flexible shaft 55 engages the top surface 26 and compressibly secures the block 25 to the upper face 14 of the plate 12.

In the embodiment shown in FIG. 13 at least one side surface 28 of a radiation treatment block 25 has a groove 29 present therein. It is recognized that the clamping device 40 shown in FIG. 13 can be used to affix a radiation treatment block 25 without a groove 29 positioned therein, to an upper face 14 of a plate 12. The threaded end portion 56 of the flexible shaft 55 can be inserted in a mounting hole 15 or slot 16 positioned proximate to at least one side surface 28 of a radiation treatment block 25. A threaded nut 43 can be positioned on the threaded end portion 56 of the flexible shaft 55. The flexible shaft 55 can be flexed until the substantially hook shaped end portion 57 of the flexible shaft 55 is positioned above and adjacent to the top surface 26 of the radiation treatment block 25. The threaded nut 43 can be adjusted on the threaded end portion 56 until at least part of the substantially hook shaped end portion 57 of the flexible shaft 55 engages the top surface 26 of the radiation treatment block 25 and compressibly secures the radiation treatment block 25 to the upper face 14 of the plate 12.

It is also recognized that the flexible shaft 55 of the clamping device 40 can optionally be provided with a substantially lever shaped end portion 50 instead of a substantially hook shaped end portion 57. The substantially lever shaped end portion 50 and the flexible shaft 55 forming an angle α. The angle α being between about 60 degrees and about 120 degrees and is preferably about 90 degrees.

In the embodiment shown, a compressible washer 49 is positioned on the flexible shaft 55 and is located at least partially between the upper face 14 of the plate 12 and the bottom surface 27 of the radiation treatment block 25.

FIG. 14 shows an alternative embodiment of a clamping device 40. The embodiment of the clamping device 40 shown in FIG. 14 is comprised of a bent shaft 58 and a threaded nut 43. The bent shaft 58 has a threaded end portion 59 and an opposite end portion sized and shaped to engage the top surface 26 of the radiation treatment block 25. In the embodiment shown in FIG. 14 the opposite end portion is a substantially hook shaped end portion 60. The threaded end portion 59 can be inserted into a mounting hole 15 or slot 16 (shown in FIG. 11) in the plate 12 that is located proximate to a groove 29 present in a side surface 28 of a radiation treatment block 25. A threaded nut 43 can be positioned on the threaded end portion 59. The bent shaft 58 can be manipulated so that the substantially hook shaped end portion 60 of the bent shaft 58 is positioned above the top surface 26 of the radiation treatment block 25 and the bent shaft 58 is positioned at least partially within a groove 29. The threaded nut 43 can be adjusted on the threaded end portion 59 so that the substantially hook shaped end portion 60 of the bent shaft 59 engages the top surface 26 of the radiation treatment block 25 and compressibly secures the radiation treatment block 25 to the upper face 14 of the plate 12.

In an alternative embodiment, the clamping device 40 shown in FIG. 14 can be used to affix a radiation treatment blocks 25 without a groove 29 positioned therein to an upper face 14 of a plate 12. The threaded end portion 59 of the bent shaft 58 can be inserted in a mounting hole 15 or slot 16 positioned proximate at least one side surface 28 of a radiation treatment block 25. A threaded nut 43 can be positioned on the threaded end portion 59 of the bent shaft 58. The bent shaft 58 can be manipulated until the substantially hook shaped end portion 60 of the bent shaft 58 is positioned above and adjacent to the top surface 26 of the radiation treatment block 25. The threaded nut 43 can be adjusted until at least part of the substantially hook shaped end portion 60 of the bent shaft 58 engages the top surface 26 of the radiation treatment block 25 and compressibly secures the radiation treatment block 25 to the upper face 14 of the plate 12.

It is also recognized that the bent shaft 58 of clamping device 40 can be fabricated with a substantially lever shaped end portion 50 instead of a substantially hook shaped end portion 60. The substantially lever shaped end portion 50 and the bent shaft 58 forming an angle α. The angle α being between about 60 degrees and about 120 degrees and is preferably about 90 degrees.

In the embodiment shown, a compressible washer 49 is positioned on the bent shaft 58 and is positioned at least partially between the upper face 14 of the plate 12 and the bottom surface 27 of the radiation treatment block 25.

FIG. 15 shows an alternative embodiment of a releasable fastener 13. The releasable fastener 13 is comprised of a rod 75, a rigid washer 65 and a threaded nut 76. Both end portions of the rod 75 are threaded, one end portion is positioned through an orifice 17 present in the plate 12 and is inserted into a threaded bore 6 (shown in FIG. 10) present in the frame body 2. The rigid washer 65 has a diameter greater than the orifice 17 and can be positioned over the exposed threaded end portion of the rod 75 such that the exposed threaded end portion of the rod 75 projects through a hole in the rigid washer 65. The rigid washer 65 rests on the upper face 14 of the plate 12. The threaded nut 76 can be adjusted on the exposed threaded end portion of the rod 75 until the threaded nut 76 engages the rigid washer 65 and compressibly secures the plate 12 to the frame body 2.

FIG. 16 shows the frame body 2 having a rail 95 mounted on a lower frame body member 4 to adapt a dimension of a frame body 2 of an adjustable radiation treatment block mounting tray 1 to fit a radiation machine 150 and demonstrates how a rail 95 can be mounted on an upper frame body member 3. Rails 95 can be mounted to the upper and lower frame body members 3, 4 by positioning a fastener 52, such as a screw, through a hole 53 present in the rail 95 and inserting an end of the fastener 52 into a rail mounting bore 11. The fastener 52 is then adjusted to secure the rail 95 to the upper and lower frame body members 3, 4.

It is recognized by those skilled in the art that, depending on the radiation machine 150 being utilized, no rail 95 may be required, a different size rail 95 may be required, or an additional rail 95 may be necessary. A rail 95 can also be affixed to the upper frame body member 3 or, optionally, to both the upper and lower frame body members 3, 4. A rail 95 can be fabricated from metal or other rigid material including but not limited to wood, plastic, fiberglass, carbon fiber or composite. A rail 95 can be marked or colored to correlate said rail 95 to a particular manufacturer or model number of a radiation machine 150.

Figure 17:
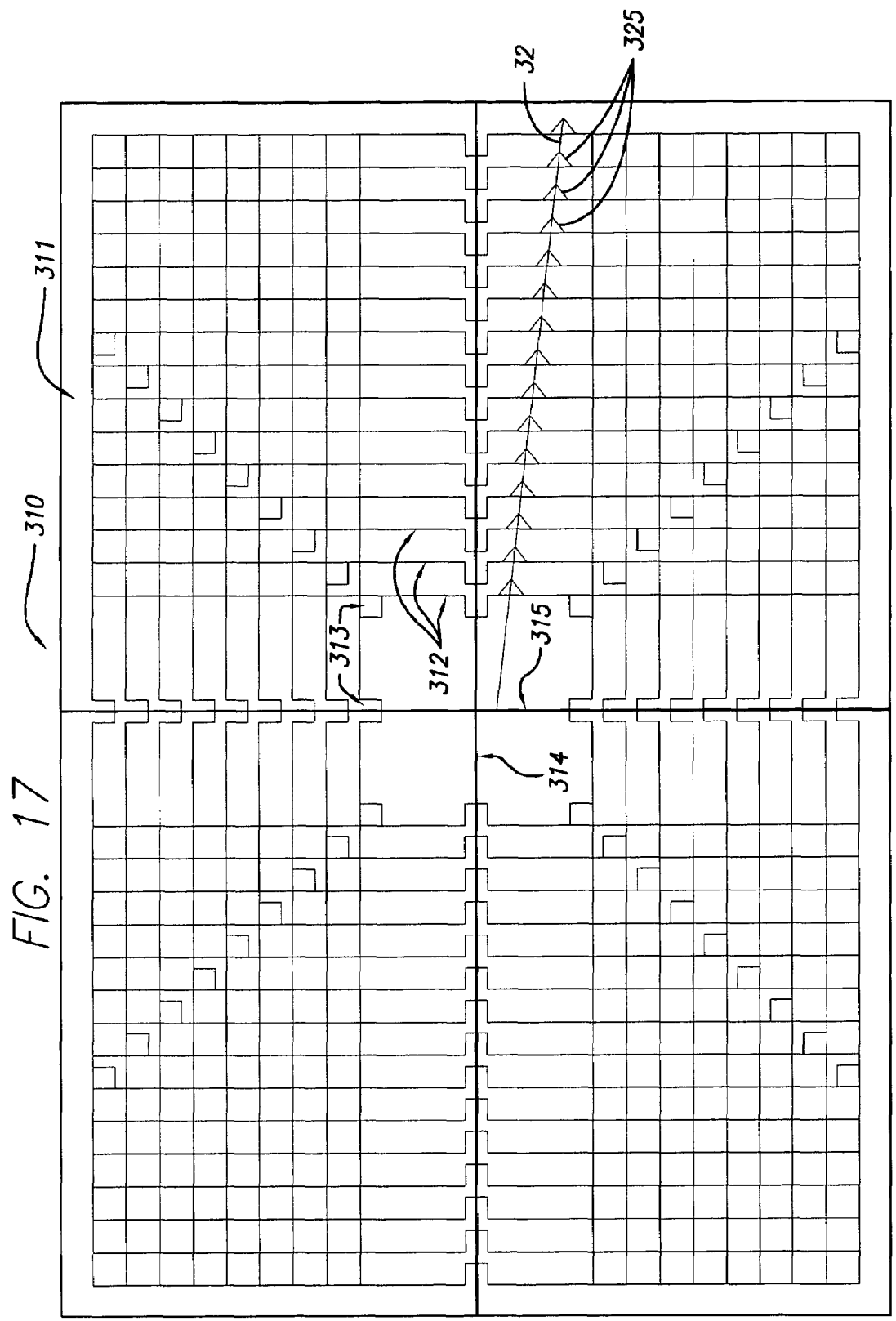
FIG. 17 shows a template that can be used with a foam block cutting machine to produce a form to cast a radiation treatment block.

FIG. 17 shows a template 310 for use with a foam block cutting machine for making a form to cast a radiation treatment block 25. In the embodiment shown, the template 310 is made from a transparent sheet 311. In the embodiment shown, the template 310 is made from a sheet 311 of plastic, however, it is recognized that other materials such as polymers, acrylics and glass would also be suitable. Although it is preferable that the sheet 311 be transparent a non-transparent or translucent sheet can also be suitable. The transparent sheet 311 has marked or scribed thereon perimetric outlines 312 of radiation treatment blocks 25 having different sizes. This allows a radiation technologist or oncologist to select the perimetric outline 312 to correspond with the required size of a radiation treatment block 25 to be fabricated. The template 310 can be provided with a horizontal line 314 and a vertical line 315 that intersect at the center of a perimetric outline 312 present on a template 310. The horizontal and vertical lines 314 and 315 can be utilized to align the template 310 with corresponding horizontal and vertical lines 316, 317 that can be present on a light table 301 of the foam block cutting machine 300 (each shown in FIG. 18).

In the embodiment shown, each side of a perimetric outline 312 has a notch 313 positioned therein. In the embodiment shown, each corner of a plurality of perimetric outlines 312 have a notch 313 positioned therein. In the embodiment shown, the notch 313 is rectangular, however, it is recognized that the notch can also be U-shaped or V-shaped. It is recognized that the perimetric outlines 312 of radiation treatment blocks 25 present on the template 310 can be provided without notches 313 positioned therein.

The template 310 can optionally have a radiation treatment block alignment line 32 scribed or marked thereon. At an intersection of the radiation treatment block alignment line 32 with a side of a perimetric outline 312 of a radiation treatment block 25, a ridge 325 is marked or scribed on the template 310. The ridge 325 protrudes from a side of a perimetric outline 312 of a radiation treatment block 25. When a radiation technologist traces over a ridge 325 present on a perimetric outline 312 of a radiation treatment block 25, a ridge 325 will be formed in foam block 307 form that can be used to cast a radiation treatment block 25. When the radiation treatment block 25 is cast in the foam block 307 form a ridge 31 will protrude from a side surface 28 of the radiation treatment block 25.

Figure 18:
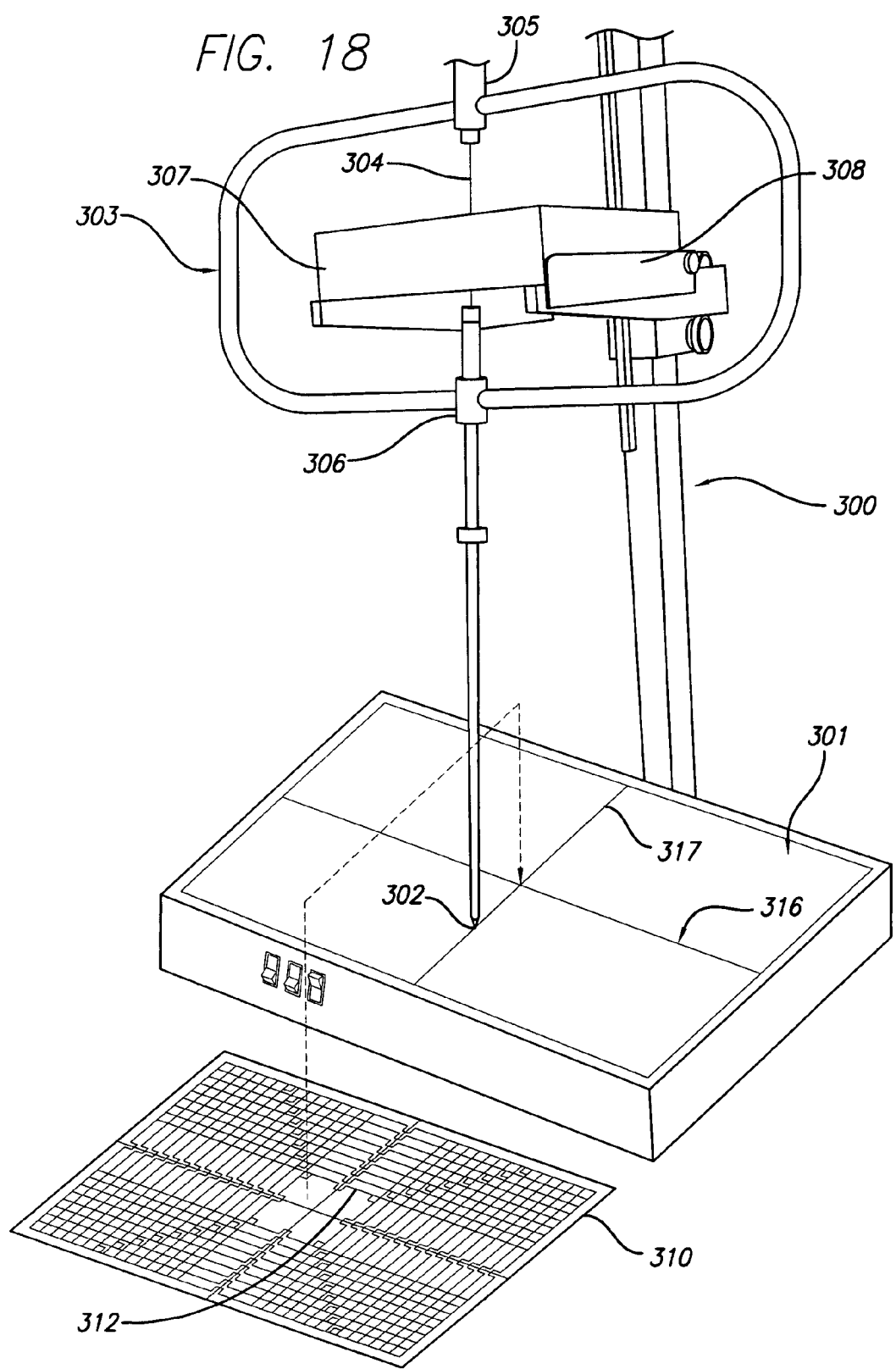
FIG. 18 shows a template that is currently in use on a commercially-available foam block cutting machine.

FIG. 18 shows a commercially-available foam block cutting machine 300 for cutting a foam form for casting a radiation treatment block 25. A template 310 for tracing a perimetric outline 312 of a radiation treatment block 25 can be placed on a light table 301 of a foam block cutting machine 300. A radiation technologist can trace a selected perimetric outline 312 of a radiation treatment block 25 on the template 310 with a stylus 302 present on the foam block cutting machine 300. The stylus 302 is connected to a hot wire frame 303 that has a hot wire 304 positioned between an upper hot wire frame member 305 and a lower hot wire frame member 306. A foam block 307 is positioned in a foam block mounting tray 308. As a radiation technologist traces a perimetric outline 312 of a radiation treatment block 25 on the template 310 the hot wire 304 cuts the foam block 307 to the same perimetric outline 312 of the radiation treatment block 25 on the template 310. If required by the prescribed treatment, the technologist can also cut the foam block 307 to create an opening in the foam block 307 that will create a beam shaping opening in the radiation treatment block 25 when a radiation treatment block 25 is cast in the foam block 307 form.

FIG. 19 shows two embodiments of a ruler 400 and 401. One embodiment of a ruler 400 has a notch 402 present therein. An alternative embodiment of a rule 401 has a tab 403 present thereon. The rulers 400 and 401 can be used by a technologist to guide a stylus 302 of a foam block cutting machine 300 while tracing a perimetric outline 312 of a radiation treatment block 25 on the template 310. The notch 402 and the tab 403 facilitate the tracing of one or more notches 313 present on a template 310. It is also recognized that a ruler 400 or 401 can have both a notch 402 and a tab 403 present therein.

The methods and apparatuses of the present invention allow radiation blocks of varying sizes to be quickly and accurately prepared using a template in conjunction with a commercially-available foam block cutting machine to cut the perimetric outline of a form for casting a radiation treatment block. A block can be mounted to a block mounting tray according to methods of this invention for the duration of the patient's treatment. Once a block is mounted, it does not have to be repeatedly handled by the technologist. If adjustments of a block in the radiation beam are required, the adjustable radiation block mounting tray of the present invention allows such adjustments to be made without further handling of the block.

Upon completion of the treatment of a patient, the radiation block can be melted and used to cast another block. This eliminates the creation of hazardous materials and waste.

What is claimed is:

1. A method for mounting at least one radiation treatment block on a radiation treatment block mounting plate comprising:
   (a) providing at least one radiation treatment block, said radiation treatment block having a top surface, a bottom surface and at least one side surface;
   (b) providing a radiation treatment block mounting plate, said radiation treatment block mounting plate having an upper face, a lower face and at least one mounting hole or slot that extends at least partially through the radiation treatment block mounting plate from its upper surface, and wherein said mounting hole or slot is positioned to permit radiation treatment blocks having different sizes to be affixed to said radiation treatment block mounting plate;
   (c) providing at least one affixing means for compressibly affixing said radiation treatment block to said radiation treatment block mounting plate, wherein said affixing means has an upper portion and a lower portion;
   (d) placing the bottom surface of said radiation treatment block on said upper face of said radiation treatment block mounting plate;
   (e) attaching said upper portion of said affixing means to said radiation treatment block;
   (f) placing said lower portion of said affixing means through said mounting hole or slot present in said radiation treatment block mounting plate;
   (g) securing said lower portion of said affixing means to said radiation treatment block mounting plate; and
   (h) adjusting said affixing means to compressibly and releasably affix said radiation treatment block to said radiation treatment block mounting plate.

2. The method of claim 1 wherein at least one mounting hole or slot extends through said radiation treatment block mounting plate from said upper face to said lower face.

3. The method of claim 1 wherein said radiation treatment block mounting plate has at least one mounting hole and at least one mounting slot.

4. The method of claim 3 wherein at least one mounting hole or slot extends through said radiation treatment block mounting plate from said upper face to said lower face.

5. The method of claim 1 wherein said upper portion of said affixing means is attached to said top surface of said radiation treatment block.

6. The method of claim 1 wherein said radiation treatment block has a ridge protruding from a side surface, said ridge extending from said top surface to said bottom surface of said radiation treatment block.

7. The method of claim 6 wherein said radiation treatment block mounting plate has a radiation treatment block alignment line marked or scribed on said upper face, said radiation treatment block alignment line positioned such that a ridge protruding from a side surface of radiation treatment blocks having different sizes is aligned over said radiation treatment block alignment line when said radiation treatment blocks are affixed to said upper face of said plate.

8. A method for mounting at least one radiation treatment block on a radiation treatment block mounting plate comprising:
   (a) providing a radiation treatment block mounting plate, said radiation treatment block mounting plate having an upper face and a lower face and at least one mounting hole or slot extending through said radiation treatment block mounting plate from said upper face to said lower face for receiving one or more external clamping means, said mounting hole or slot being positioned to allow radiation treatment blocks having different sizes to be affixed to said radiation treatment block mounting plate;
   (b) providing at least one radiation treatment block, said radiation treatment block having a top surface, a bottom surface and at least one side surface;
   (c) positioning said bottom surface of said radiation treatment block on said upper face of said radiation treatment block mounting plate;
   (d) providing external clamping means for compressibly affixing each radiation treatment block to said upper face of said radiation treatment block mounting plate;
   (e) attaching said external clamping means to said radiation treatment block mounting plate;
   (f) positioning said external clamping means on each radiation treatment block;
   (g) adjusting said external clamping means to compressibly affix said radiation treatment block to said upper face of the radiation treatment block mounting plate.

9. The method of claim 8 wherein said radiation treatment block mounting plate has at least one mounting hole and at least one mounting slot.

10. The method of claim 8 wherein said external clamping means is a clamp, a pivot clamp, a hook clamp, a toggle clamp, a nylon tie or a swing clamp.

11. The method of claim 8 wherein at least one piece of compressible material is positioned at least partially between the bottom surface of said radiation treatment block and said upper face of said radiation treatment block mounting plate.

12. The method of claim 11 wherein said compressible material is an elastomeric washer.

13. The method of claim 8 wherein said radiation treatment block has a ridge protruding from a side surface, said ridge extending from said top surface to said bottom surface of said radiation treatment block.

14. The method of claim 13 wherein said radiation treatment block mounting plate has a radiation treatment block alignment line marked or scribed on said upper face, said radiation treatment block alignment line positioned such that a ridge protruding from a side surface of radiation treatment blocks having different sizes is aligned over said radiation treatment block alignment line when said radiation treatment blocks are affixed to said upper face of said plate.

15. A method for mounting a radiation treatment block on a radiation treatment block mounting plate comprising:
   (a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;
   (b) providing at least one radiation treatment block, said radiation treatment block having a top surface, a bottom surface and at least one side surface;
   (c) providing at least one clamping device to externally affix said radiation treatment block to said radiation treatment block mounting plate, at least one clamping device having an end portion sized and shaped to fit within a mounting hole or slot for securing said clamping device to said radiation treatment block mounting plate and an opposite end portion sized and shaped to engage said top surface of said radiation treatment block;
   (d) positioning said bottom surface of said radiation treatment block on said upper face of said radiation treatment block mounting plate;
   (e) positioning said end portion of said clamping device through a mounting hole or slot and securing said clamping device to said radiation treatment block mounting plate;
   (f) positioning said opposite end portion of said clamping device above and adjacent to said top surface of said radiation treatment block; and
   (g) adjusting said clamping device until at least part of said opposite end portion of said clamping device engages said top surface of said radiation treatment block and compressibly affixes said radiation treatment block to said upper face of said radiation treatment block mounting plate.

16. The method of claim 15 wherein said radiation treatment block mounting plate has at least one mounting hole and at least one mounting slot.

17. The method of claim 15 wherein at least one piece of compressible material is positioned at least partially between said bottom surface of said radiation treatment block and said upper face of said radiation treatment block mounting plate.

18. The method of claim 17 where said compressible material is an elastomeric washer.

19. The method of claim 15 wherein said radiation treatment block has a ridge protruding from a side surface, said ridge extending from said top surface to said bottom surface of said radiation treatment block.

20. The method of claim 19 wherein said radiation treatment block mounting plate has a radiation treatment block alignment line marked or scribed on said upper face, said radiation treatment block alignment line positioned such that a ridge protruding from a side surface of radiation treatment blocks having different sizes is aligned over said radiation treatment block alignment line when said radiation treatment blocks are affixed to said upper face of said plate.

21. A method for mounting a radiation treatment block on a radiation treatment block mounting plate comprising:
   (a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;
   (b) providing at least one radiation treatment block, said radiation treatment block having a top surface, a bottom surface and at least one side surface;
   (c) providing at least one clamping device to externally affix said radiation treatment block to said radiation treatment block mounting plate, wherein at least one clamping device comprises a shaft and a threaded nut, said shaft having a threaded end portion and an opposite end portion sized and shaped to engage said top surface of said radiation treatment block;
   (d) positioning said bottom surface of said radiation treatment block on said upper face of said radiation treatment block mounting plate,
   (e) inserting said threaded end portion of said shaft through a mounting hole or slot in said radiation treatment block mounting plate, said mounting hole or slot being positioned proximate to at least one side surface of said radiation treatment block;
   (f) attaching a threaded nut onto said threaded end portion of said shaft;
   (g) positioning said shaft until said opposite end portion of said shaft is positioned above and adjacent to said top surface of said radiation treatment block;
   (h) adjusting said threaded nut on said threaded end portion of said shaft until at least part of said opposite end portion of said shaft engages said top surface of said radiation treatment block and compressibly affixes said radiation treatment block to said upper face of said radiation treatment block mounting plate.

22. The method of claim 21 wherein said radiation treatment block mounting plate has at least one mounting hole and at least one mounting slot.

23. The method of claim 21 wherein at least one piece of compressible material is positioned at least partially between said bottom surface of said radiation treatment block and said upper face of said radiation treatment block mounting plate.

24. The method of claim 21 where an elastomeric washer is provided for at least one of said clamping devices, said elastomeric washer having an opening therein, inserting said threaded end portion of said shaft through said opening and positioning said elastomeric washer at least partially between said bottom surface of said radiation treatment block and said upper face of said radiation treatment block mounting plate.

25. The method of claim 21 wherein said shaft of said clamping device is flexible.

26. The method of claim 25 wherein said opposite end portion of said shaft sized and shaped to engage said top surface of said radiation treatment block is substantially hook shaped.

27. The method of claim 25 wherein said opposite end portion of said shaft sized and shaped to engage said top surface of said radiation treatment block is a substantially lever shaped end portion, said substantially lever shaped end portion and said shaft forming an angle α, said angle α being between about 60 and about 120 degrees.

28. The method of claim 27 wherein said angle α is about 90 degrees.

29. The method of claim 21 wherein said shaft of said clamping device is bent.

30. The method of claim 29 wherein said opposite end portion of said shaft sized and shaped to engage said top surface of said radiation treatment block is substantially hook shaped.

31. The method of claim 29 wherein said opposite end portion of said shaft sized and shaped to engage said top surface of said radiation treatment block is a substantially lever shaped end portion, said substantially lever shaped end portion and said shaft forming an angle α, said angle α being between about 60 and about 120 degrees.

32. The method of claim 31 wherein said angle α is about 90 degrees.

33. The method of claim 21 wherein said radiation treatment block has a ridge protruding from a side surface, said ridge extending from said top surface to said bottom surface of said radiation treatment block.

34. The method of claim 33 wherein said radiation treatment block mounting plate has a radiation treatment block alignment line marked or scribed on said upper face, said radiation treatment block alignment line positioned such that a ridge protruding from a side surface of radiation treatment blocks having different sizes is aligned over said radiation treatment block alignment line when said radiation treatment blocks are affixed to said upper face of said plate.

35. A method for mounting a radiation treatment block on a radiation treatment block mounting plate comprising:
(a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;
(b) providing at least one radiation treatment block, said radiation treatment block having a top surface, a bottom surface and at least one side surface, at least one side surface having at least one groove positioned therein, said groove extending from said top surface to said bottom surface and projecting from said side surface into said radiation treatment block, said groove being sized and shaped to allow a shaft of a clamping device to fit at least partially within said groove;
(c) providing at least one clamping device to externally affix said radiation treatment block to said radiation treatment block mounting plate, wherein at least one clamping device comprises a shaft and a threaded nut, said shaft having a threaded end portion and an opposite end portion sized and shaped to engage said top surface of said radiation treatment block;
(d) positioning said bottom surface of said radiation treatment block on said upper face of said radiation treatment block mounting plate;
(e) inserting said threaded end portion of said shaft through a mounting hole or slot in said radiation treatment block mounting plate, said mounting hole or slot being positioned proximate to a groove in a side surface of said radiation treatment block;
(f) attaching a threaded nut onto said threaded end portion of said shaft;
(g) positioning said shaft of said clamping device until said shaft is positioned at least partially in said groove and said opposite end portion of said shaft is positioned above and adjacent to said top surface of said radiation treatment block;
(h) adjusting said threaded nut on said threaded end portion of said shaft until at least part of said opposite end portion of said shaft engages said top surface of said radiation treatment block and compressibly affixes said radiation treatment block to said upper face of said radiation treatment block mounting plate.

36. The method of claim 35 wherein said radiation treatment block mounting plate has at least one mounting hole and at least one mounting slot.

37. The method of claim 35 wherein at least one piece of compressible material is positioned at least partially between said bottom surface of said radiation treatment block and said upper face of said radiation treatment block mounting plate.

38. The method of claim 35 where an elastomeric washer is provided for at least one of said clamping devices, said elastomeric washer having an opening therein, inserting said threaded end portion of said shaft through said opening and positioning said elastomeric washer at least partially between said bottom surface of said radiation treatment block and said upper face of said radiation treatment block mounting plate.

39. The method of claim 35 wherein said groove is rectangular shaped.

40. The method of claim 35 wherein said groove is U-shaped.

41. The method of claim 35 wherein said groove is V-shaped.

42. The method of claim 35 wherein said radiation treatment block has four side surfaces.

43. The method of claim 35 wherein each side surface has at least one groove positioned therein.

44. The method of claim 35 wherein said shaft of said clamping device is flexible.

45. The method of claim 44 wherein said opposite end portion of said shaft is substantially hook shaped.

46. The method of claim 44 wherein said opposite end portion of said shaft is a substantially lever shaped end portion, said substantially lever shaped end portion and said shaft forming an angle α, said angle α being between about 60 and about 120 degrees.

47. The method of claim 46 wherein said angle α is about 90 degrees.

48. The method of claim 35 wherein said shaft of said clamping device is bent.

49. The method of claim 48 wherein said opposite end portion of said shaft is substantially hook shaped.

50. The method of claim 48 wherein said opposite end portion of said shaft is a substantially lever shaped end portion, said substantially lever shaped end portion and said shaft forming an angle α, said angle α being between about 60 and about 120 degrees.

51. The method of claim 50 wherein said angle α is about 90 degrees.

52. The method of claim 35 wherein said radiation treatment block has a ridge protruding from a side surface, said ridge extending from said top surface to said bottom surface of said radiation treatment block.

53. The method of claim 52 wherein said radiation treatment block mounting plate has a radiation treatment block alignment line marked or scribed on said upper face, said radiation treatment block alignment line positioned such that a ridge protruding from a side surface of radiation treatment blocks having different sizes is aligned over said radiation treatment block alignment line when said radiation treatment blocks are affixed to said upper face of said plate.

54. A method for mounting a radiation treatment block on a radiation treatment block mounting plate comprising:
  (a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;
  (b) providing at least one radiation treatment block, said radiation treatment block having a top surface, a bottom surface and at least one side surface;
  (c) providing at least one clamping device to externally affix said radiation treatment block to said radiation treatment block mounting plate, at least one clamping device comprising a rod, a shaft, and a threaded nut, said rod having one end portion hingeably connected to said shaft and an opposite threaded end portion, said shaft having an end portion hingeably connected to said rod and an opposite end portion sized and shaped to engage said top surface of said radiation treatment block;
  (d) positioning said bottom surface of said radiation treatment block on said upper face of said radiation treatment block mounting plate,
  (e) inserting said threaded end portion of said rod of said clamping device through a mounting hole or slot in said radiation treatment block mounting plate, said mounting hole or slot being positioned proximate to at least one side surface of said radiation treatment block;
  (f) attaching a threaded nut onto said threaded end portion of said rod;
  (g) pivoting said shaft of said clamping device until said opposite end portion of said shaft is positioned above and adjacent to said top surface of said radiation treatment block;
  (h) adjusting said threaded nut on said threaded end portion of said rod until at least part of said opposite end portion of said shaft engages said top surface of said radiation treatment block and compressibly affixes said radiation treatment block to said upper face of said radiation treatment block mounting plate.

55. The method of claim 54 wherein said radiation treatment block mounting plate has at least one mounting hole and at least one mounting slot.

56. The method of claim 54 wherein at least one piece of compressible material is positioned at least partially between said bottom surface of said radiation treatment block and said upper face of said radiation treatment block mounting plate.

57. The method of claim 54 where an elastomeric washer is provided for at least one of said clamping devices, said elastomeric washer having an opening therein, inserting said threaded end portion of said rod through said opening and positioning said elastomeric washer at least partially between said bottom surface of said radiation treatment block and said upper face of said radiation treatment block mounting plate.

58. The method of claim 54 wherein said radiation treatment block has four side surfaces.

59. The method of claim 54 wherein said opposite end portion of said shaft is substantially hook shaped.

60. The method of claim 54 wherein said opposite end portion of said shaft is a substantially lever shaped end portion, said substantially lever shaped end portion and said shaft forming an angle $\alpha$, said angle $\alpha$ being between about 60 and about 120 degrees.

61. The method of claim 60 wherein said angle $\alpha$ is about 90 degrees.

62. The method of claim 54 wherein said radiation treatment block has a ridge protruding from a side surface, said ridge extending from said top surface to said bottom surface of said radiation treatment block.

63. The method of claim 62 wherein said radiation treatment block mounting plate has a radiation treatment block alignment line marked or scribed on said upper face, said radiation treatment block alignment line positioned such that a ridge protruding from a side surface of radiation treatment blocks having different sizes is aligned over said radiation treatment block alignment line when said radiation treatment blocks are affixed to said upper face of said plate.

64. A method for mounting a radiation treatment block on a radiation treatment block mounting plate comprising:
  (a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;
  (b) providing at least one radiation treatment block, said radiation treatment block having a top surface, a bottom surface, and at least one side surface, at least one side surface having at least one groove positioned therein, said groove extending from said top surface to said bottom surface and projecting from said side surface into said radiation treatment block, said groove being sized and shaped to allow a shaft of a clamping device to fit at least partially within said groove;
  (c) providing at least one clamping device to externally affix said radiation treatment block to said radiation treatment block mounting plate, at least one clamping device comprising a rod, a shaft, and a threaded nut, said rod having one end portion hingeably connected to said shaft and an opposite threaded end portion, said shaft having an end portion hingeably connected to said rod and an opposite end portion sized and shaped to engage said top surface of said radiation treatment block;
  (d) positioning said bottom surface of said radiation treatment block on said upper face of said radiation treatment block mounting plate;
  (e) inserting said threaded end portion of said rod of said clamping device through a mounting hole or slot in said radiation treatment block mounting plate, said mounting hole or slot being positioned proximate to a groove in a side surface of said radiation treatment block;

(f) attaching a threaded nut onto said threaded end portion of said rod;

(g) pivoting said shaft of said clamping device until said shaft is positioned at least partially in a groove in a side surface of said radiation treatment block and said opposite end portion of said shaft is positioned above and adjacent to said top surface of said radiation treatment block;

(h) adjusting said nut on said threaded end portion of said rod until at least part of said opposite end portion of said shaft engages said top surface of said radiation treatment block and compressibly affixes said radiation treatment block to said upper face of said radiation treatment block mounting plate.

65. The method of claim 64 wherein said radiation treatment block mounting plate has at least one mounting hole and at least one mounting slot.

66. The method of claim 64 wherein at least one piece of compressible material is positioned at least partially between said bottom surface of said radiation treatment block and said upper face of said radiation treatment block and said mounting face.

67. The method of claim 64 where an elastomeric washer is provided for at least one of said clamping devices, said elastomeric washer having an opening therein, inserting said threaded end portion of said rod through said opening and positioning said elastomeric washer at least partially between said bottom surface of said radiation treatment block and said upper face of said radiation treatment block mounting plate.

68. The method of claim 64 wherein said groove is rectangular shaped.

69. The method of claim 64 wherein said groove is U-shaped.

70. The method of claim 64 wherein said groove is V-shaped.

71. The method of claim 64 wherein said radiation treatment block has four side surfaces.

72. The method of claim 64 wherein said opposite end portion of said shaft is substantially hook shaped.

73. The method of claim 64 wherein said opposite end portion of said shaft is a substantially lever shaped end portion, said substantially lever shaped end portion and said shaft forming an angle $\alpha$, said angle $\alpha$ being between about 60 and about 120 degrees.

74. The method of claim 73 wherein said angle $\alpha$ is about 90 degrees.

75. The method of claim 64 wherein each side surface has at least one groove positioned therein.

76. The method of claim 64 wherein said radiation treatment block has a ridge protruding from a side surface, said ridge extending from said top surface to said bottom surface of said radiation treatment block.

77. The method of claim 76 wherein said radiation treatment block mounting plate has a radiation treatment block alignment line marked or scribed on said upper face, said radiation treatment block alignment line positioned such that a ridge protruding from a side surface of radiation treatment blocks having different sizes is aligned over said radiation treatment block alignment line when said radiation treatment blocks are affixed to said upper face of said plate.

78. A method for mounting a radiation treatment block on a radiation treatment block mounting plate comprising:

(a) providing a radiation treatment block mounting plate, said radiation treatment block mounting plate having an upper face and a lower face, said radiation treatment block mounting plate further having a plurality of mounting holes or slots extending through said radiation treatment block mounting plate from said upper face to said lower face for receiving a clamping device, said mounting holes or slots being positioned to allow radiation treatment blocks having different sizes to be affixed to said radiation treatment block mounting plate;

(b) providing at least one radiation treatment block, said radiation treatment block having a top surface, a bottom surface, and four side surfaces, each side surface having a groove positioned therein, said groove extending from said top surface to said bottom surface and projecting from said side surface into said radiation treatment block, said groove being sized and shaped to allow a shaft of a clamping device to fit at least partially within said groove;

(c) providing four clamping devices to externally affix said radiation treatment block to said radiation treatment block mounting plate, each clamping device comprising a rod, a shaft, and a threaded nut, said rod having one end portion hingeably connected to said shaft and an opposite threaded end portion, said shaft having an end portion hingeably connected to said rod and an opposite substantially hook shaped end portion;

(d) positioning said bottom surface of said radiation treatment block on said upper face of said radiation treatment block mounting plate;

(e) inserting said threaded end portion of each rod of each clamping device through a mounting hole or slot in said radiation treatment block mounting plate, said mounting hole or slot being positioned proximate to a groove in a side surface of said radiation treatment block;

(f) attaching a threaded nut onto said threaded end portion of each rod;

(g) pivoting said shaft of each clamping device until said shaft is positioned at least partially in a groove in a side surface of said radiation treatment block and said substantially hook shaped end portion of each shaft is positioned above and adjacent to said top surface of said radiation treatment block;

(h) adjusting said nut on said threaded end portion of each rod until at least part of each substantially hook shaped end portion of each shaft engages said top surface of said radiation treatment block and compressibly affixes said radiation treatment block to said upper face of said radiation treatment block mounting plate.

79. The method of claim 78 wherein said radiation treatment block mounting plate has at least one mounting hole and at least one mounting slot.

80. The method of claim 78 wherein at least one piece of compressible material is positioned at least partially between said bottom surface of said radiation treatment block and said upper face of said radiation treatment block mounting plate.

81. The method of claim 78 where an elastomeric washer is provided for each of said clamping devices, each elastomeric washer having an opening therein, inserting said threaded end portion of said rod through said opening and positioning each elastomeric washer at least partially between said bottom surface of said radiation treatment block and said upper face of said radiation treatment block mounting plate.

82. The method of claim 78 wherein said groove is rectangular shaped.

83. The method of claim 78 wherein said groove is U-shaped.

84. The method of claim 78 wherein said groove is V-shaped.

85. The method of claim 78 wherein said radiation treatment block has a ridge protruding from a side surface, said ridge extending from said top surface to said bottom surface of said radiation treatment block.

86. The method of claim 85 wherein said radiation treatment block mounting plate has a radiation treatment block alignment line marked or scribed on said upper face, said radiation treatment block alignment line positioned such that a ridge protruding from a side surface of radiation treatment blocks having different sizes is aligned over said radiation treatment block alignment line when said radiation treatment blocks are affixed to said upper face of said plate.

87. A method for mounting a radiation treatment block on a radiation treatment block mounting plate comprising:
- (a) providing a radiation treatment block mounting plate, said radiation treatment block mounting plate having an upper face and a lower face, said radiation treatment block mounting plate having at least one mounting hole or slot extending through said radiation treatment block mounting plate from said upper face to said lower face for receiving a clamping device, said mounting hole or slot being positioned to allow radiation treatment blocks having different sizes to be affixed to said radiation treatment block mounting plate;
- (b) providing at least one radiation treatment block, said radiation treatment block having a top surface, a bottom surface and at least three side surfaces, the intersection of a side surface with another side surface forming a corner edge, said radiation treatment block having a groove positioned on at least one corner edge, said groove extending from said top surface to said bottom surface and projecting from said corner edge into said radiation treatment block, said groove sized and shaped to allow a shaft of a clamping device to fit at least partially within said groove;
- (c) providing at least one clamping device to externally affix said radiation treatment block to said radiation treatment block mounting plate, said clamping device comprising a rod, a shaft, and a threaded nut, said rod having one end portion hingeably connected to said shaft and an opposite threaded end portion, said shaft having an end portion hingeably connected to said rod and an opposite end portion shaped and sized to engage said top surface of said radiation treatment block;
- (d) positioning said bottom surface of said radiation treatment block on said upper face of said radiation treatment block mounting plate;
- (e) inserting said threaded end portion of said rod of said clamping device through a mounting hole or slot in said radiation treatment block mounting plate, said mounting hole or slot positioned proximate to a groove in a corner edge;
- (f) attaching a threaded nut onto said threaded end portion of said rod;
- (g) pivoting said shaft of said clamping device until said opposite end portion of said shaft is positioned above and adjacent to said top surface of said radiation treatment block; and
- (h) adjusting said nut on said threaded end portion of said rod until at least part of said opposite end portion of said shaft engages said top surface of said radiation treatment block and compressibly affixes said radiation treatment block to said upper face of said radiation treatment block mounting plate.

88. The method of claim 87 wherein said radiation treatment block mounting plate has at least one mounting hole and at least one mounting slot.

89. The method of claim 87 wherein at least one piece of compressible material is positioned at least partially between said bottom surface of said radiation treatment block and said upper face of said radiation treatment block mounting plate.

90. The method of claim 87 where an elastomeric washer is provided for at least one of said clamping devices, said elastomeric washer having an opening therein, inserting said threaded end portion of said rod through said opening and positioning said elastomeric washer at least partially between said bottom surface of said radiation treatment block and said upper face of said radiation treatment block mounting plate.

91. The method of claim 87 wherein said opposite end portion of said shaft is substantially hook shaped.

92. The method of claim 87 wherein said opposite end portion of said shaft is a substantially lever shaped end portion, said substantially lever shaped end portion and said shaft forming an angle α, said angle α being between about 60 and about 120 degrees.

93. The method of claim 92 wherein said angle α is about 90 degrees.

94. The method of claim 87 wherein said groove is rectangular shaped.

95. The method of claim 87 wherein said groove is U-shaped.

96. The method of claim 87 wherein said groove is V-shaped.

97. The method of claim 87 wherein said radiation treatment block has a ridge protruding from a side surface, said ridge extending from said top surface to said bottom surface of said radiation treatment block.

98. The method of claim 97 wherein said radiation treatment block mounting plate has a radiation treatment block alignment line marked or scribed on said upper face, said radiation treatment block alignment line positioned such that a ridge protruding from a side surface of radiation treatment blocks having different sizes is aligned over said radiation treatment block alignment line when said radiation treatment blocks are affixed to said upper face of said plate.

99. A method for mounting a radiation treatment block on a radiation treatment block mounting plate comprising:
- (a) providing a radiation treatment block mounting plate, said radiation treatment block mounting plate having an upper face and a lower face, said radiation treatment block mounting plate having a plurality of mounting holes or slots extending through said radiation treatment block mounting plate from said upper face to said lower face for receiving a clamping device, said mounting holes or slots being positioned to allow radiation treatment blocks having different sizes to be affixed to said radiation treatment block mounting tray;
- (b) providing at least one radiation treatment block, said radiation treatment block having a top surface, a bottom surface and at least three side surfaces, the intersection of a side surface with another side surface forming a corner edge, said radiation treatment block having a groove positioned on at least one corner edge, said groove extending from said top surface to said bottom surface and projecting from said corner edge into said radiation treatment block, said groove sized and shaped to allow a shaft of a clamping device to fit at least partially within said groove;

(c) providing at least one clamping device to externally affix said radiation treatment block to said radiation treatment block mounting plate, said clamping device comprising a shaft and a threaded nut, said shaft having a threaded end portion and an opposite end portion sized and shaped to engage said top surface of the radiation treatment block;

(d) positioning said bottom surface of said radiation treatment block on said upper face of said radiation treatment block mounting plate;

(e) inserting said threaded end portion of said shaft of said clamping device through a mounting hole or slot in said radiation treatment block mounting plate, said mounting hole or slot positioned proximate to a groove in a corner edge;

(f) attaching a threaded nut onto said threaded end portion of said shaft;

(g) positioning said shaft of said clamping device until said shaft is positioned at least partially in said groove and said opposite end portion of said shaft is positioned above and adjacent to said top surface of radiation treatment block;

(h) adjusting said threaded nut on said threaded end portion of said shaft until at least part of said opposite end portion of said shaft engages said top surface of said radiation treatment block and compressibly affixes said radiation treatment block to said upper face of said radiation treatment block mounting plate.

100. The method of claim 99 wherein said radiation treatment block mounting plate has at least one mounting hole and at least one mounting slot.

101. The method of claim 99 wherein at least one piece of compressible material is positioned at least partially between said bottom surface of said radiation treatment block and said upper face of said radiation treatment block mounting plate.

102. The method of claim 99 where an elastomeric washer is provided for at least one of said clamping devices, said elastomeric washer having an opening therein, inserting said threaded end portion of said rod through said opening and positioning said elastomeric washer at least partially between said bottom surface of said radiation treatment block and said upper face of said radiation treatment block mounting plate.

103. The method of claim 99 wherein said shaft of said clamping device is flexible.

104. The method of claim 103 wherein said opposite end portion of said shaft is substantially hook shaped.

105. The method of claim 103 wherein said opposite end portion of said shaft is a substantially lever shaped end portion, said substantially lever shaped end portion and said shaft forming an angle α, said angle α being between about 60 and about 120 degrees.

106. The method of claim 105 wherein said angle α is about 90 degrees.

107. The method of claim 99 wherein said shaft of said clamping device is bent.

108. The method of claim 107 wherein said opposite end portion of said shaft is substantially hook shaped.

109. The method of claim 107 wherein said opposite end portion of said shaft is a substantially lever shaped end portion, said substantially lever shaped end portion and said shaft forming an angle α, said angle α being between about 60 degrees and about 120 degrees.

110. The method of claim 109 wherein said angle α is about 90 degrees.

111. The method of claim 99 wherein said groove is rectangular shaped.

112. The method of claim 99 wherein said groove is U-shaped.

113. The method of claim 99 wherein said groove is V-shaped.

114. The method of claim 99 wherein said radiation treatment block has a ridge protruding from a side surface, said ridge extending from said top surface to said bottom surface of said radiation treatment block.

115. The method of claim 114 wherein said radiation treatment block mounting plate has a radiation treatment block alignment line marked or scribed on said upper face, said radiation treatment block alignment line positioned such that a ridge protruding from a side surface of radiation treatment blocks having different sizes is aligned over said radiation treatment block alignment line when said radiation treatment blocks are affixed to said upper face of said plate.

116. A method for mounting a radiation treatment block on a radiation treatment block mounting plate comprising:

(a) providing a radiation treatment block mounting plate, said radiation treatment block mounting plate having an upper face and a lower face, said radiation treatment block mounting plate further having at least one mounting hole or slot extending through said radiation treatment block mounting plate from said upper face to said lower face for receiving an external clamping device, said mounting hole or slot positioned to allow the mounting of radiation treatment blocks having different sizes to said radiation treatment block mounting plate;

(b) providing at least one radiation treatment block, said radiation treatment block having a top surface, a bottom surface, and at least one side surface, at least one side surface having at least one groove positioned therein, said groove extending from said top surface to said bottom surface and projecting from said side surface into said radiation treatment block, said groove being sized and shaped to allow a shaft of a clamping device to fit at least partially within said groove;

(c) providing at least one clamping device to externally affix said radiation treatment block to said radiation treatment block mounting plate, at least one clamping device comprising a rod, a shaft, and a threaded nut, said rod having one end portion hingeably connected to said shaft and an opposite threaded end portion, said shaft having an end portion hingeably connected to said rod and an opposite oversized end portion, at least one dimension of said oversized end portion being greater than a dimension of said groove;

(d) positioning said bottom surface of said radiation treatment block on said upper face of said radiation treatment block mounting plate;

(e) inserting said threaded end portion of said rod of said clamping device through a mounting hole or slot in said radiation treatment block mounting plate, said mounting hole or slot being positioned proximate to a groove in a side surface of said radiation treatment block;

(f) attaching a threaded nut onto said threaded end portion of said rod;

(g) pivoting said shaft of said clamping device until said shaft is positioned at least partially in a groove in a side surface of said radiation treatment block and said oversized end portion of said shaft is positioned above and adjacent to said top surface of said radiation treatment block;

(h) adjusting said nut on said threaded end portion of said rod until said oversized end portion of said shaft engages said top surface of said radiation treatment block or one or more face of said groove and compressibly affixes said radiation treatment block to said upper face of said radiation treatment block mounting plate.

117. The method of claim 116 wherein said radiation treatment block mounting plate has at least one mounting hole and at least one mounting slot.

118. The method of claim 116 wherein said radiation treatment block has a ridge protruding from a side surface, said ridge extending from said top surface to said bottom surface of said radiation treatment block.

119. The method of claim 118 wherein said radiation treatment block mounting plate has a radiation treatment block alignment line marked or scribed on said upper face, said radiation treatment block alignment line positioned such that a ridge protruding from a side surface of radiation treatment blocks having different sizes is aligned over said radiation treatment block alignment line when said radiation treatment blocks are affixed to said upper face of said plate.

120. An adjustable radiation treatment block mounting tray comprising:
(a) a substantially rigid frame body having a top face and a bottom face, an upper frame body member, a lower frame body member, and opposing side frame body members, said frame body having a generally central opening;
(b) a plate having an upper face and a lower face, said lower face of said plate being positioned on said top face of said frame body, said plate having at least one radiation treatment block mounting hole or slot extending through said plate from said upper face to said lower face for use in mounting a radiation treatment block to said upper face of said plate;
(c) means to releasably secure said plate to said frame body, said means allowing said plate to move relative to said frame body when in a released position and when in a fastened position said means compressibly secures said plate to said frame body.

121. The adjustable radiation treatment block mounting tray as in claim 120 wherein said plate has at least one mounting hole and at least one mounting slot.

122. The adjustable radiation treatment block mounting tray as in claim 120 wherein said means to releasably secure said plate to said frame body is a clamp, a cam clamp, a threaded fastener, a bolt and nut, or a screw.

123. The adjustable radiation treatment block mounting tray as in claim 122 wherein said screw is a thumb screw, a knurled head screw, or a knob screw.

124. The adjustable radiation treatment block mounting tray as in claim 120 wherein said plate has a radiation treatment block alignment line marked or scribed on said upper face of said plate, said radiation treatment block alignment line positioned such that a ridge protruding from a side surface of a radiation treatment block is aligned over said radiation treatment block alignment line when said radiation treatment block is affixed to said upper face of said plate.

125. An adjustable radiation treatment block mounting tray comprising:
(a) a substantially rigid frame body having a top face and a bottom face, an upper frame body member, a lower frame body member, and opposing side frame body members, said frame body having a generally central opening, and at least one bore for receiving a releasable fastener therein;
(b) a plate having an upper face and a lower face, said lower face of said plate being positioned on said top face of said frame body, said plate having at least one mounting hole or slot extending through said plate from said upper face to said lower face for use in mounting a radiation treatment block to said upper face of said plate, and at least one orifice extending through said plate from said upper face to said lower face, with at least one orifice being positioned over at least one bore in said frame body;
(c) at least one releasable fastener to releasably secure said plate to said frame body, said releasable fastener having a head portion at one end and a shank portion at an opposite end, said shank portion of each releasable fastener being positioned through an orifice in said plate and inserted into a bore in said frame body, wherein a diameter of said orifice is larger than a diameter of said shank portion to allow said plate to move relative to said frame body when said releasable fastener is in a released position, a diameter of said head portion being larger than a diameter of said orifice such that when said releasable fastener is in a fastened position said head portion compressibly secures said plate to said frame body.

126. The adjustable radiation treatment block mounting tray as in claim 125 wherein said plate has at least one mounting hole and at least one mounting slot.

127. The adjustable radiation treatment block mounting tray as in claim 125 wherein at least one bore in said frame body is threaded.

128. The adjustable radiation treatment block mounting tray as in claim 125 wherein said releasable fastener is a screw, a thumb screw, a knurled head screw, a knob screw, an adjustable diameter pin, a cam clamp, or a bolt.

129. The adjustable radiation treatment block mounting tray as in claim 125 wherein said plate has four orifices.

130. The adjustable radiation treatment block mounting tray as in claim 125 further comprising at least one spring attachment fitting affixed to said top face of said upper frame body member, at least one spring attachment fitting affixed to said upper face of said plate, and a spring, said spring connecting a spring attachment fitting affixed to said top face of said upper frame body member to a spring attachment fitting affixed to said upper face of said plate.

131. The adjustable radiation treatment block mounting tray as in claim 130 wherein said spring attachment fitting is a screw, a bolt, or a rod.

132. The adjustable radiation treatment block mounting tray as in claim 125 wherein said plate has one or more notch positioned on at least one outer edge of said plate, said notch positioned to align over a spring attachment fitting affixed to said frame body.

133. The adjustable radiation treatment block mounting tray as in claim 125 wherein said frame body or said plate or optionally both said frame body and said plate has at least one measuring gauge positioned thereon to allow an extent of movement of said plate relative to said frame to be observably measured.

134. The adjustable radiation treatment block mounting tray as in claim 125 further comprising a plurality of rail mounting bores in said upper frame body or lower frame body members and optionally in both upper and lower frame body members for receiving a fastener therein, at least one rail positioned on said upper frame body member or lower frame body member and optionally on both upper and lower frame body members, each rail extending beyond an outer edge of said upper or lower frame body member to adapt a dimension of said frame body to fit within a radiation treatment machine, each rail having a plurality of rail mounting holes for receiving a fastener there through, each rail being affixed to said upper or lower frame by at least one fastener that extends through a rail mounting hole and into a rail mounting bore in said upper or lower frame body member.

135. The adjustable radiation treatment block mounting tray as in claim 134 wherein said fastener is a releasable fastener to releasably affix said rail on said upper or lower frame body member.

136. The adjustable radiation treatment block mounting tray as in claim 134 wherein said rail has one or more identifying mark or color that correlates said rail to a particular manufacturer or model number of a radiation machine.

137. The adjustable radiation treatment block mounting tray as in claim 125 wherein said frame body has a slotted orifice positioned in at least one side frame body member, said slotted orifice forming a handle portion in said side frame body member, said handle portion optionally having at least one hole present therein for mounting one or more handle fitting thereto.

138. The adjustable radiation treatment block mounting tray as in claim 125 wherein said plate has a radiation treatment block alignment line marked or scribed on said upper face of said plate, said radiation treatment block alignment line positioned such that a ridge protruding from a side surface of a radiation treatment block is aligned over said radiation treatment block alignment line when said radiation treatment block is affixed to said upper face of said plate.

139. An adjustable radiation treatment block mounting tray comprising:
  (a) a substantially rigid frame body, said frame body having a top face and a bottom face, an upper frame body member, a lower frame body member, and opposing side frame body members, a generally central opening and least one bore for receiving a releasable fastener therein;
  (b) a plate having an upper face and a lower face, said lower face of said plate being positioned on said top face of said frame body, said plate having at least one mounting hole or slot extending through said plate from said upper face to said lower face for use in mounting a radiation treatment block to said upper face of said plate and at least one orifice extending through said plate from said upper face to said lower face, with at least one orifice being positioned over at least one bore in said frame body;
  (c) at least one releasable fastener to releasably secure said plate to said frame body, said releasable fastener having a head portion at one end, a shank portion at an opposite end and a washer positioned on said shank portion adjoining said head portion, said shank portion of each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said washer being greater than a diameter of said orifice such that when said releasable fastener is in a fastened position said releasable fastener and washer compressibly secure said plate to said frame body.

140. The adjustable radiation treatment block mounting tray as in claim 139 wherein said plate has at least one mounting hole and at least one mounting slot.

141. The adjustable radiation treatment block mounting tray as in claim 139 wherein at least one bore is threaded.

142. The adjustable radiation treatment block mounting tray as in claim 139 wherein said releasable fastener is a screw, a thumb screw, a knurled head screw, a knob screw, an adjustable diameter pin, a cam clamp, or a bolt.

143. The adjustable radiation treatment block mounting tray as in claim 139 wherein said plate has four orifices.

144. The adjustable radiation treatment block mounting tray as in claim 139 further comprising at least one spring attachment fitting affixed to said top face of said upper frame body member, at least one spring attachment fitting affixed to said upper face of said plate, and a spring, said spring connecting a spring attachment fitting affixed to said top face of said upper frame body member to a spring attachment fitting affixed to said upper face of said plate.

145. The adjustable radiation treatment block mounting tray as in claim 144 wherein said spring attachment fitting is a screw, a bolt, or a rod.

146. The adjustable radiation treatment block mounting tray as in claim 139 wherein said plate has one or more notch positioned on at least one outer edge of said plate, said notch being positioned to align over a spring attachment fitting affixed to said frame body.

147. The adjustable radiation treatment block mounting tray as in claim 139 wherein said frame body or said plate or optionally both said frame body and said plate has at least one measuring gauge positioned thereon to allow an extent of movement of the plate relative to the frame to be observably measured.

148. The adjustable radiation treatment block mounting tray as in claim 139 further comprising a plurality of rail mounting bores in said upper frame body or lower frame body members and optionally in both upper and lower frame body members for receiving a fastener therein, at least one rail positioned on said upper frame body member or lower frame body member and optionally on both upper and lower frame body members, each rail extending beyond an outer edge of said upper or lower frame body member to adapt a dimension of said frame body to fit within a radiation treatment machine, each rail having a plurality of rail mounting holes for receiving a fastener there through, each rail being affixed to said upper or lower frame by at least one fastener that extends through a rail mounting hole and into a rail mounting bore in said upper or lower frame body member.

149. The adjustable radiation treatment block mounting tray as in claim 148 wherein said fastener is a releasable fastener to releasably affix said rail on said upper or lower frame body members.

150. The adjustable radiation treatment block mounting tray as in claim 148 wherein said rail has one or more identifying mark or color that correlate said rail to a particular manufacturer or model number of a radiation machine.

151. The adjustable radiation treatment block mounting tray as in claim 139 wherein said frame body has a slotted orifice positioned in at least one side frame body member, said slotted orifice forming a handle portion in said side frame body member, said handle portion optionally having at least one hole present therein for mounting one or more handle fitting thereto.

152. The adjustable radiation treatment block mounting tray as in claim 139 wherein said plate has a radiation treatment block alignment line marked or scribed on said upper face of said plate, said radiation treatment block alignment line positioned such that a ridge protruding from a side surface of a radiation treatment block is aligned over said radiation treatment block alignment line when said radiation treatment block is affixed to said upper face of said plate.

153. An adjustable radiation treatment block mounting tray comprising:
(a) a substantially rigid frame body, said frame body having a top face and a bottom face, an upper frame body member, a lower frame body member, opposing side frame body members, a generally central opening, and a plurality of bores for receiving a releasable fastener therein;
(b) a plate having an upper face and a lower face, said lower face of said plate being positioned on said top face of said frame body, said plate having at least one mounting hole or slot extending through said plate from said upper face to said lower face for use in mounting a radiation treatment block to said upper face of said plate, and four orifices extending through said plate from said upper face to said lower face, each orifice positioned over a bore in said frame body;
(c) four releasable fasteners to releasably secure said plate to said frame body, each releasable fastener having a head portion at one end, a shank portion at an opposite end and a washer positioned on said shank portion adjoining said head portion, each shank portion of each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said washer being greater than a diameter of said orifice such that when said releasable fastener is in a fastened position, said releasable fasteners and washers compressibly secure said plate to said frame body.

154. The adjustable radiation treatment block mounting tray as in claim 153 wherein said plate has at least one mounting hole and at least one mounting slot.

155. The adjustable radiation treatment block mounting tray as in claim 153 wherein at least one bore in said frame body is threaded.

156. The adjustable radiation treatment block mounting tray as in claim 153 wherein said releasable fastener is a screw, a thumb screw, a knurled head screw, a knob screw, an adjustable diameter pin, a cam clamp, or a bolt.

157. The adjustable radiation treatment block mounting tray as in claim 153 further comprising at least one spring attachment fitting affixed to said top face of said upper frame body member, at least one spring attachment fitting affixed to said upper face of said plate, and a spring, said spring connecting a spring attachment fitting affixed to said top face of said upper frame body member to a spring attachment fitting affixed to said upper face of said plate.

158. The adjustable radiation treatment block mounting tray as in claim 157 wherein said spring attachment fitting is a screw, a bolt, or a rod.

159. The adjustable radiation treatment block mounting tray as in claim 153 wherein said plate has one or more notch positioned on at least one outer edge of said plate, said notch positioned to align over a spring attachment fitting affixed to said frame body.

160. The adjustable radiation treatment block mounting tray as in claim 153 wherein said frame body or said plate or optionally both said frame body and said plate has at least one measuring gauge positioned thereon to allow the extent of movement of the plate relative to the frame to be observably measured.

161. The adjustable radiation treatment block mounting tray as in claim 153 further comprising a plurality of rail mounting bores in the upper frame body or lower frame body members and optionally in both upper and lower frame body members for receiving a fastener therein, at least one rail positioned on said upper frame body member or lower frame body member and optionally on both upper and lower frame body members, each rail extending beyond an outer edge of said upper or lower frame body member to adapt a dimension of said frame body so as to fit within a radiation treatment machine, each rail having a plurality of rail mounting holes for receiving a fastener there through, each rail being affixed to said upper or lower frame by at least one fastener that extends through a rail mounting hole and into a rail mounting bore in said upper or lower frame body member.

162. The adjustable radiation treatment block mounting tray as in claim 161 wherein said fastener is a releasable fastener to releasably affix said rail on said upper or lower frame body members.

163. The adjustable radiation treatment block mounting tray as in claim 161 wherein said rail has one or more identifying mark or color that correlate said rail to a particular manufacturer or model number of a radiation machine.

164. The adjustable radiation treatment block mounting tray as in claim 153 wherein said frame body has a slotted orifice positioned in at least one side frame body member, said slotted orifice forming a handle portion in said side frame body member, said handle portion optionally having at least one hole present therein for mounting one or more handle fitting thereto.

165. The adjustable radiation treatment block mounting tray as in claim 153 wherein said plate has a radiation treatment block alignment line marked or scribed on said upper face of said plate, said radiation treatment block alignment line positioned such that a ridge protruding from a side surface of a radiation treatment block is aligned over said radiation treatment block alignment line when said radiation treatment block is affixed to said upper face of said plate.

166. An adjustable radiation treatment block mounting tray comprising:
(a) a substantially rigid frame body having a top face and a bottom face, an upper frame body member, a lower frame body member, and opposing side frame body members, said frame body having a generally central opening, and at least one bore for receiving a releasable fastener therein;
(b) a plate having an upper face and a lower face, said bottom face of said frame body being positioned on said upper face of said plate, said plate having at least one mounting hole or slot extending through said plate from said upper face to said lower face for use in mounting a radiation treatment block to said upper face of said plate, and at least one orifice extending through said plate from said upper face to said lower face, with at least one orifice being positioned over at least one bore in said frame body;
(c) at least one releasable fastener to releasably secure said plate to said frame body, said releasable fastener having a head portion at one end and a shank portion at an opposite end, said shank portion of each releasable fastener being positioned through an orifice in said plate and inserted into a bore in said frame body, wherein a diameter of said orifice is larger than a diameter of said shank portion to allow said plate to move relative to said frame body when said releasable fastener is in a released position, a diameter of said head portion being larger than a diameter of said orifice such that when said releasable fastener is in a fastened position said head portion compressibly secures said plate to said frame body.

167. The adjustable radiation treatment block mounting tray as in claim 166 wherein said plate has at least one mounting hole and at least one mounting slot.

168. The adjustable radiation treatment block mounting tray as in claim 166 wherein said plate has a radiation treatment block alignment line marked or scribed on said upper face of said plate, said radiation treatment block alignment line positioned such that a ridge protruding from a side surface of a radiation treatment block is aligned over said radiation treatment block alignment line when said radiation treatment block is affixed to said upper face of said plate.

169. An adjustable radiation treatment block mounting tray comprising:
(a) a substantially rigid frame body, said frame body having a top face and a bottom face, an upper frame body member, a lower frame body member, and opposing side frame body members, a generally central opening and least one bore for receiving a releasable fastener therein;
(b) a plate having an upper face and a lower face, said bottom face of said frame body being positioned on said upper face of said plate, said plate having at least one mounting hole or slot extending through said plate from said upper face to said lower face for use in mounting a radiation treatment block to said upper face of said plate and at least one orifice extending through said plate from said upper face to said lower face, with at least one orifice being positioned over at least one bore in said frame body;
(c) at least one releasable fastener to releasably secure said plate to said frame body, said releasable fastener having a head portion at one end, a shank portion at an opposite end and a washer positioned on said shank portion adjoining said head portion, said shank portion of each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said washer being greater than a diameter of said orifice such that when said releasable fastener is in a fastened position said releasable fastener and washer compressibly secure said plate to said frame body.

170. The adjustable radiation treatment block mounting tray as in claim 169 wherein said plate has at least one mounting hole and at least one mounting slot.

171. The adjustable radiation treatment block mounting tray as in claim 169 wherein said plate has a radiation treatment block alignment line marked or scribed on said upper face of said plate, said radiation treatment block alignment line positioned such that a ridge protruding from a side surface of a radiation treatment block is aligned over said radiation treatment block alignment line when said radiation treatment block is affixed to said upper face of said plate.

172. An adjustable radiation treatment block mounting tray comprising:
(a) a plate having an upper face and a lower face, said plate having at least one mounting hole or slot extending through said plate from said upper face to said lower face for use in mounting a radiation treatment block to said upper face, said plate further having a plurality of bores for receiving a releasable fastener therein;
(b) a substantially rigid frame body having a top face and a bottom face, said bottom face of said frame body being positioned on said upper face of said plate, said frame body having an upper frame body member, a lower frame body member, and opposing side frame body members, said frame body having a generally central opening, said frame body further having at least one orifice extending through said frame body from said top face to said bottom face, at least one orifice being positioned over at least one bore in said plate;
(c) at least one releasable fastener to releasably secure said frame body to said plate, said fastener having a head portion at one end and a shank portion at an opposite end, said shank portion of each releasable fastener being positioned through an orifice in said frame body and inserted into a bore in said plate, a diameter of said orifice being larger than a diameter of said shank portion to allow said frame body to move relative to said plate when said releasable fastener is in a released position, a diameter of said head portion being larger than a diameter of said orifice such that when said releasable fastener is in a fastened position said head portion compressibly secures said frame body to said plate.

173. The adjustable radiation treatment block mounting tray as in claim 172 wherein said plate has at least one mounting hole and at least one mounting slot.

174. The adjustable radiation treatment block mounting tray as in claim 172 wherein at least one bore in said plate is threaded.

175. The adjustable radiation treatment block mounting tray as in claim 172 wherein said releasable fastener is a screw, a thumb screw, a knurled head screw, a knob screw, an adjustable diameter pin, a cam clamp, or a bolt.

176. The adjustable radiation treatment block mounting tray as in claim 172 wherein said plate has a radiation treatment block alignment line marked or scribed on said upper face of said plate, said radiation treatment block alignment line positioned such that a ridge protruding from a side surface of a radiation treatment block is aligned over said radiation treatment block alignment line when said radiation treatment block is affixed to said upper face of said plate.

177. An adjustable radiation treatment block mounting tray comprising:
(a) a plate having an upper face and a lower face, said plate having at least one mounting hole or slot extending through said plate from said upper face to said lower face for use in mounting a radiation treatment block to said upper face, said plate further having a plurality of bores for receiving a releasable fastener therein;
(b) a substantially rigid frame body having a top face and a bottom face, said bottom face of said frame body being positioned on said upper face of said plate, said frame body having an upper frame body member, a lower frame body member, opposing side frame body members, said frame body having a generally central opening, said frame body further having at least one orifice extending through said frame body from said top face to said bottom face, at least one orifice being positioned such that said orifice is aligned over at least one bore in said plate;

(c) at least one releasable fastener to releasably secure said frame body to said plate, said releasable fastener having a head portion at one end, a shank portion at an opposite end and a washer positioned on said shank portion adjoining said head portion, said shank portion of each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said washer being greater than a diameter of said orifice such that when said releasable fastener is in a fastened position said releasable fastener and washer compressibly secure said frame body to said plate.

178. The adjustable radiation treatment block mounting tray as in claim 177 wherein said plate has at least one mounting hole and at least one mounting slot.

179. The adjustable radiation treatment block mounting tray as in claim 177 wherein said plate has a radiation treatment block alignment line marked or scribed on said upper face of said plate, said radiation treatment block alignment line positioned such that a ridge protruding from a side surface of a radiation treatment block is aligned over said radiation treatment block alignment line when said radiation treatment block is affixed to said upper face of said plate.

180. An adjustable radiation treatment block mounting tray comprising:
(a) a substantially rigid frame body, said frame body having a top face and a bottom face, an upper frame body member, a lower frame body member, and opposing side frame body members, said frame body having a generally central opening, said frame body further having a plurality of threaded bores for receiving a threaded rod therein;
(b) a plate having an upper face and a lower face, said lower face of said plate being positioned on said top face of said frame body, said plate having at least one mounting hole or slot extending through said plate from said upper face to said lower face for use in mounting a radiation treatment block to said upper face, said plate further having at least one orifice extending through said plate from said upper face to said lower face, at least one orifice being positioned over at least one threaded bore in said frame body;
(c) at least one rod having opposing end portions, both of said end portions of said rod being threaded, one end portion of said rod being inserted into a threaded bore in said frame body, an opposite exposed end portion of said rod being positioned through an orifice in said plate, a diameter of said rod being less than a diameter of said orifice in said plate, a threaded nut being attached to said exposed end portion of said rod, a diameter of said nut being greater than a diameter of said orifice such that when said nut is in a fastened position said nut compressibly secures said plate to said frame body and when said nut is in a released position allowing said plate to move relative to said frame body.

181. The adjustable radiation treatment block mounting tray as in claim 180 wherein said plate has at least one mounting hole and at least one mounting slot.

182. The adjustable radiation treatment block mounting tray as in claim 180 wherein said plate has a radiation treatment block alignment line marked or scribed on said upper face of said plate, said radiation treatment block alignment line positioned such that a ridge protruding from a side surface of a radiation treatment block is aligned over said radiation treatment block alignment line when said radiation treatment block is affixed to said upper face of said plate.

183. An adjustable radiation treatment block mounting tray comprising:
(a) a substantially rigid frame body, said frame body having a top face and a bottom face, an upper frame body member, a lower frame body member, and opposing side frame body members, said frame body having a generally central opening, said frame body further having a plurality of threaded bores for receiving a threaded rod therein;
(b) a plate having an upper face and a lower face, said lower face of said plate being positioned on said top face of said frame body, said plate having at least one mounting hole or slot extending through said plate from said upper face to said lower face for use in mounting a radiation treatment block to said upper face, said plate further having at least one orifice extending through said plate from said upper face to said lower face, at least one orifice being positioned over at least one threaded bore in said frame body;
(c) at least one rod having opposing end portions, both of said end portions of said rod being threaded, one end portion of said rod being inserted into a threaded bore in said frame body, an opposite exposed end portion of said rod being positioned through an orifice in said plate, a diameter of said rod being less than a diameter of an orifice in said plate, a washer being positioned over said exposed end portion of said rod and positioned on said upper face of said plate, a diameter of said washer being greater than a diameter of said orifice, a nut being attached to said exposed end portion of said rod, such that when said nut is in a fastened position said nut and washer compressibly secure said plate to said frame body and when said nut is in a released position allowing said plate to move relative to said frame body.

184. The adjustable radiation treatment block mounting tray as in claim 183 wherein said plate has at least one mounting hole and at least one mounting slot.

185. The adjustable radiation treatment block mounting tray as in claim 183 wherein said plate has a radiation treatment block alignment line marked or scribed on said upper face of said plate, said radiation treatment block alignment line positioned such that a ridge protruding from a side surface of a radiation treatment block is aligned over said radiation treatment block alignment line when said radiation treatment block is affixed to said upper face of said plate.

186. An adjustable radiation treatment block mounting tray comprising:
(a) a substantially rigid frame body, said frame body having a top face and a bottom face, an upper frame body member, a lower frame body member, and opposing side frame body members, said frame body having a generally central opening, said frame body further having at least one tray adjustment slot extending through said frame body from said top face to said bottom face;

(b) a plate having an upper face and a lower face, said lower face of said plate being positioned on said top face of said frame body, said plate having at least one mounting hole or slot extending through said plate from said upper face to said lower face for use in mounting a radiation treatment block to said upper face, said plate further having at least one tray adjustment slot extending through said plate from said upper face to said lower face, at least one tray adjustment slot in said plate being generally perpendicular to a tray adjustment slot in said frame body and being positioned to overlap a tray adjustment slot in said frame body;

(c) at least one releasable fastener to releasably secure said plate to said frame body, said releasable fastener having a head portion at one end, a shank portion at an opposite end, said shank portion of each releasable fastener positioned through both a tray adjustment slot in said plate and a tray adjustment slot in said frame body wherein when said releasable fastener is in a fastened position said releasable fastener compressibly secures said plate to said frame body and when said releasable fastener is in a released position said releasable fastener allows said plate to move relative to said frame body.

187. The adjustable radiation treatment block mounting tray as in claim 186 wherein said plate has at least one mounting hole and at least one mounting slot.

188. The adjustable radiation treatment block mounting tray as in claim 186 wherein said releasable fastener is a bolt and nut, a screw and nut or a cam clamp and nut.

189. The adjustable radiation treatment block mounting tray as in claim 188 wherein said nut is a T-nut, a wing nut, a lock nut, a finger nut, a knurled nut, a handle nut, or a push nut.

190. The adjustable radiation treatment block mounting tray as in claim 188 wherein said screw is a thumb screw, a knurled head screw or a knob screw.

191. The adjustable radiation treatment block mounting tray as in claim 186 wherein said plate has a radiation treatment block alignment line marked or scribed on said upper face of said plate, said radiation treatment block alignment line positioned such that a ridge protruding from a side surface of a radiation treatment block is aligned over said radiation treatment block alignment line when said radiation treatment block is affixed to said upper face of said plate.

192. A method for adjusting a radiation treatment block in a radiation beam comprising:

(a) providing a radiation treatment block mounted on a plate of an adjustable radiation treatment block mounting tray, said adjustable radiation treatment block mounting tray being installed on a radiation treatment machine, said adjustable treatment block mounting tray comprising:

a substantially rigid frame body having a top face and a bottom face, an upper frame body member, a lower frame body member, and opposing side frame body members, said frame body having a generally central opening;

a plate having an upper face and a lower face, said lower face of said plate being positioned on said top face of said frame body, said plate having at least one mounting hole or slot extending through said plate from said upper face to said lower face for use in mounting a radiation treatment block to said upper face of said plate;

means to releasably secure said plate to said frame body, said means allowing said plate to move relative to said frame body when said means is in a released position and when said means is in a fastened position said means compressibly securing said plate to said frame body;

(b) adjusting said means to a released position so that said plate and said radiation treatment block affixed thereto can move relative to said frame body;

(c) aligning said radiation treatment block within said radiation beam by moving said plate until said radiation treatment block is correctly aligned within said radiation beam for a prescribed treatment of a patient;

(d) adjusting said means to a fastened position compressibly securing said plate to said frame body and securing said radiation treatment block within said radiation beam.

193. The method as in claim 192 wherein said plate has at least one mounting hole and at least one mounting slot.

194. The method as in claim 192 wherein said means to releasably secure said plate to said frame body is a clamp.

195. A method for adjusting a radiation treatment block in a radiation beam comprising:

(a) providing a radiation treatment block mounted on a plate of an adjustable radiation treatment block mounting tray, said adjustable radiation treatment block mounting tray being installed on a radiation treatment machine, said adjustable radiation treatment block mounting tray comprising:

a substantially rigid frame body having a top face and a bottom face, an upper frame body member, a lower frame body member, and opposing side frame body members, said frame body having a generally central opening, said frame body further having at least one bore for receiving a releasable fastener therein;

a plate having an upper face and a lower face, said lower face of said plate being positioned on said top face of said frame body, said plate having at least one mounting hole or slot extending through said plate from said upper face to said lower face for use in mounting a radiation treatment block to said upper face of said plate, said plate further having at least one orifice extending through said plate from said upper face to said lower face, at least one orifice being positioned over at least one bore in said frame body;

at least one releasable fastener to releasably secure said plate to said frame body, at least one releasable fastener having a head portion at one end, a shank portion at an opposite end, said shank portion of said each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said head portion being greater than a diameter of said orifice such that when said releasable fastener is in a fastened position said head portion compressibly secures said plate to said frame body;

(b) adjusting each releasable fastener to a released position so that said plate and said radiation treatment block affixed thereto can move relative to said frame body;

(c) aligning said radiation treatment block within said radiation beam by moving said plate until said radiation treatment block is correctly aligned within said radiation beam for a prescribed treatment of a patient;

(d) adjusting at least one releasable fastener until said releasable fastener is in a fastened position compressibly securing said plate to said frame body and securing said radiation treatment block within said radiation beam.

196. The method as in claim 195 wherein said plate has at least one mounting hole and at least one mounting slot.

197. A method for adjusting a radiation treatment block in a radiation treatment beam comprising:
  (a) providing a radiation treatment block mounted on a plate of an adjustable radiation treatment block mounting tray, said adjustable radiation treatment block mounting tray being installed on a radiation treatment machine, said adjustable radiation treatment block mounting tray comprising:
    a substantially rigid frame body having a top face and a bottom face, an upper frame body member, a lower frame body member, and opposing side frame body members, said frame body having a generally central opening, said frame body further having at least one bore for receiving a releasable fastener therein;
    a plate having an upper face and a lower face, said lower face being positioned on said top face of said frame body, said plate having at least one mounting hole or slot extending through said plate from said upper face to said lower face for use in mounting a radiation treatment block to said upper face, said plate further having at least one orifice extending through said plate from said upper face to said lower face, at least one orifice being positioned over at least one bore in said frame body;
    at least one releasable fastener to releasably secure said plate to said frame body, at least one releasable fastener having a head portion at one end, a shank portion at an opposite end and a washer positioned on said shank portion adjoining said head portion, said shank portion of each releasable fastener being positioned through an orifice in said plate and inserted into a bore in said frame body, a diameter of said orifice being larger than a diameter of said shank portion to allow said plate to move relative to said frame body when said releasable fastener is in a released position, a diameter of said washer being greater than a diameter of said orifice such that when said releasable fastener is in a fastened position said releasable fastener and washer compressibly secure said plate to said frame body;
  (b) adjusting each releasable fastener to a released position so that said plate and radiation treatment block can move relative to said frame body;
  (c) aligning said radiation treatment block within said radiation beam by moving said plate until said radiation treatment block is correctly aligned within said radiation beam for a prescribed treatment of a patient;
  (d) adjusting at least one releasable fastener until said fastener is in a fastened position compressibly securing said plate to said frame body and securing said radiation treatment block within said radiation beam.

198. The method as in claim 197 wherein said plate has at least one mounting hole and at least one mounting slot.

* * * * *